（12） United States Patent
Kusk et al.

(10) Patent No.: US 12,396,957 B2
(45) Date of Patent: *Aug. 26, 2025

(54) CELL LINES AND THEIR USE IN ENCAPSULATED CELL BIODELIVERY

(71) Applicant: GLORIANA THERAPEUTICS SARL, Geneva (CH)

(72) Inventors: Philip Kusk, Lynge (DK); Lars Ulrik Wahlberg, Bristol, RI (US)

(*) Notice: Subject to any disclaimer, the term of this patent is extended or adjusted under 35 U.S.C. 154(b) by 959 days.

This patent is subject to a terminal disclaimer.

(21) Appl. No.: 17/145,877

(22) Filed: Jan. 11, 2021

(65) Prior Publication Data

US 2021/0128482 A1    May 6, 2021

Related U.S. Application Data

(63) Continuation of application No. 15/851,741, filed on Dec. 22, 2017, now Pat. No. 10,888,526, which is a continuation of application No. 14/821,498, filed on Aug. 7, 2015, now Pat. No. 9,884,023, which is a continuation of application No. 14/289,856, filed on May 29, 2014, now Pat. No. 9,121,037, which is a continuation of application No. 13/145,669, filed as
(Continued)

(30) Foreign Application Priority Data

Jan. 23, 2009   (DK) .................. PA 2009 00103
Sep. 22, 2009   (DK) .................. PA 2009 70121

(51) Int. Cl.
C12N 15/88    (2006.01)
A61K 9/48     (2006.01)
A61K 38/18    (2006.01)
A61K 38/22    (2006.01)
C12N 15/90    (2006.01)
A61K 35/12    (2015.01)
A61K 48/00    (2006.01)

(52) U.S. Cl.
CPC .......... *A61K 9/4816* (2013.01); *A61K 9/4808* (2013.01); *A61K 9/4866* (2013.01); *A61K 38/185* (2013.01); *A61K 38/22* (2013.01); *C12N 15/88* (2013.01); *C12N 15/90* (2013.01); *C12N 15/907* (2013.01); *A61K 2035/126* (2013.01); *A61K 48/00* (2013.01); *C12N 2800/90* (2013.01)

(58) Field of Classification Search
None
See application file for complete search history.

(56) References Cited

U.S. PATENT DOCUMENTS 6,361,771 B1 * 3/2002 Tao .................. A61K 38/185
                                           623/4.1

FOREIGN PATENT DOCUMENTS

WO    WO 2008/079608    *  7/2008  ............. C12N 15/63

OTHER PUBLICATIONS

Chung et al., Proc. Natl. Acad. Sci. USA (PNAS), vol. 94, pp. 575-580, Jan. 1997 (Year: 1997).*

* cited by examiner

*Primary Examiner* — Evelyn Y Pyla
(74) *Attorney, Agent, or Firm* — Feeney IP Law; Alan F Feeney; Logan D Faucher

(57) ABSTRACT

The present invention relates to generation of cell lines expressing recombinant proteins for use in naked and encapsulated cell biodelivery of secreted therapeutic molecules. In one embodiment the cell line is human. In another aspect of the invention the transposon system is used for generating a cell line for secretion of a biologically active polypeptide.

11 Claims, 3 Drawing Sheets

Specification includes a Sequence Listing.

Related U.S. Application Data application No. PCT/DK2010/050013 on Jan. 21, 2010, now Pat. No. 8,741,340.

(60) Provisional application No. 61/244,993, filed on Sep. 23, 2009, provisional application No. 61/146,754, filed on Jan. 23, 2009.

SEQUENCE LISTING

<160> NUMBER OF SEQ ID NOS: 16

<210> SEQ ID NO 1
<211> LENGTH: 412
<212> TYPE: DNA
<213> ORGANISM: Homo sapiens

<400> SEQUENCE: 1

```
atgaagtgca gctgggtgat cttcttcctg atggcagtgg ttacaggtaa ggggctccca      60
agtcccaaac ttgagggtcc ataaactctg tgacagtggc aatcactttg ccttcttttc     120
tacagggtg aattcgggct ggaccctgaa cagcgcgggc tacctgctgg gccctcacgc      180
cgtgggcaac cacagaagct tcagcgacaa gaacggcctg accagcaagc gggagctgcg     240
gcccgaggac gacatgaagc ccggcagctt cgacagaagc atccccgaga acaacatcat     300
gcggaccatc atcgagtttc tgagctttct gcacctgaaa gaggccggag ccctggaccg     360
gctgctggat ctgcctgccg ctgcctcctc agaagacatc gagcggtcct ga             412
```

<210> SEQ ID NO 2
<211> LENGTH: 110
<212> TYPE: PRT
<213> ORGANISM: Homo sapiens

<400> SEQUENCE: 2

```
Met Lys Cys Ser Trp Val Ile Phe Phe Leu Met Ala Val Val Thr Gly
1               5                   10                  15

Val Asn Ser Gly Trp Thr Leu Asn Ser Ala Gly Tyr Leu Leu Gly Pro
            20                  25                  30

His Ala Val Gly Asn His Arg Ser Phe Ser Asp Lys Asn Gly Leu Thr
        35                  40                  45

Ser Lys Arg Glu Leu Arg Pro Glu Asp Asp Met Lys Pro Gly Ser Phe
    50                  55                  60

Asp Arg Ser Ile Pro Glu Asn Asn Ile Met Arg Thr Ile Ile Glu Phe
65                  70                  75                  80

Leu Ser Phe Leu His Leu Lys Glu Ala Gly Ala Leu Asp Arg Leu Leu
                85                  90                  95

Asp Leu Pro Ala Ala Ala Ser Ser Glu Asp Ile Glu Arg Ser
            100                 105                 110
```

<210> SEQ ID NO 3
<211> LENGTH: 726
<212> TYPE: DNA
<213> ORGANISM: Homo sapiens
<220> FEATURE:
<221> NAME/KEY: CDS
<222> LOCATION: (1)..(726)

<400> SEQUENCE: 3

```
atg tcc atg ttg ttc tac act ctg atc aca gct ttt ctg atc ggc ata      48
Met Ser Met Leu Phe Tyr Thr Leu Ile Thr Ala Phe Leu Ile Gly Ile
1               5                   10                  15 cag gcg gaa cca cac tca gag agc aat gtc cct gca gga cac acc atc      96
Gln Ala Glu Pro His Ser Glu Ser Asn Val Pro Ala Gly His Thr Ile
            20                  25                  30 ccc caa gtc cac tgg act aaa ctt cag cat tcc ctt gac act gcc ctt     144
Pro Gln Val His Trp Thr Lys Leu Gln His Ser Leu Asp Thr Ala Leu
        35                  40                  45 cgc aga gcc cgc agc gcc ccg gca gcg gcg ata gct gca cgc gtg gcg     192
Arg Arg Ala Arg Ser Ala Pro Ala Ala Ala Ile Ala Ala Arg Val Ala
    50                  55                  60
```

```
ggg cag acc cgc aac att act gtg gac ccc agg ctg ttt aaa aag cgg        240
Gly Gln Thr Arg Asn Ile Thr Val Asp Pro Arg Leu Phe Lys Lys Arg
 65              70              75              80 cga ctc cgt tca ccc cgt gtg ctg ttt agc acc cag cct ccc cgt gaa        288
Arg Leu Arg Ser Pro Arg Val Leu Phe Ser Thr Gln Pro Pro Arg Glu
             85              90              95 gct gca gac act cag gat ctg gac ttc gag gtc ggt ggt gct gcc ccc        336
Ala Ala Asp Thr Gln Asp Leu Asp Phe Glu Val Gly Gly Ala Ala Pro
         100             105             110 ttc aac agg act cac agg agc aag cgg tca tca tcc cat ccc atc ttc        384
Phe Asn Arg Thr His Arg Ser Lys Arg Ser Ser Ser His Pro Ile Phe
     115             120             125 cac agg ggc gaa ttc tcg gtg tgt gac agt gtc agc gtg tgg gtt ggg        432
His Arg Gly Glu Phe Ser Val Cys Asp Ser Val Ser Val Trp Val Gly
 130             135             140 gat aag acc acc gcc aca gac atc aag ggc aag gag gtg atg gtg ttg        480
Asp Lys Thr Thr Ala Thr Asp Ile Lys Gly Lys Glu Val Met Val Leu
145             150             155             160 gga gag gtg aac att aac aac agt gta ttc aaa cag tac ttt ttt gag        528
Gly Glu Val Asn Ile Asn Asn Ser Val Phe Lys Gln Tyr Phe Phe Glu
                 165             170             175 acc aag tgc cgg gac cca aat ccc gtt gac agc ggg tgc cgg ggc att        576
Thr Lys Cys Arg Asp Pro Asn Pro Val Asp Ser Gly Cys Arg Gly Ile
             180             185             190 gac tca aag cac tgg aac tca tat tgt acc acg act cac acc ttt gtc        624
Asp Ser Lys His Trp Asn Ser Tyr Cys Thr Thr Thr His Thr Phe Val
         195             200             205 aag gcg ctg acc atg gat ggc aag cag gct gcc tgg cgg ttt atc cgg        672
Lys Ala Leu Thr Met Asp Gly Lys Gln Ala Ala Trp Arg Phe Ile Arg
     210             215             220 ata gat acg gcc tgt gtg tgt gtg ctc agc agg aag gct gtg aga aga        720
Ile Asp Thr Ala Cys Val Cys Val Leu Ser Arg Lys Ala Val Arg Arg
225             230             235             240 gcc tga                                                                726
Ala

<210> SEQ ID NO 4
<211> LENGTH: 241
<212> TYPE: PRT
<213> ORGANISM: Homo sapiens

<400> SEQUENCE: 4

Met Ser Met Leu Phe Tyr Thr Leu Ile Thr Ala Phe Leu Ile Gly Ile
 1               5                  10                  15

Gln Ala Glu Pro His Ser Glu Ser Asn Val Pro Ala Gly His Thr Ile
             20                  25                  30

Pro Gln Val His Trp Thr Lys Leu Gln His Ser Leu Asp Thr Ala Leu
         35                  40                  45

Arg Arg Ala Arg Ser Ala Pro Ala Ala Ala Ile Ala Ala Arg Val Ala
     50                  55                  60

Gly Gln Thr Arg Asn Ile Thr Val Asp Pro Arg Leu Phe Lys Lys Arg
 65              70                  75                  80

Arg Leu Arg Ser Pro Arg Val Leu Phe Ser Thr Gln Pro Pro Arg Glu
                 85                  90                  95

Ala Ala Asp Thr Gln Asp Leu Asp Phe Glu Val Gly Gly Ala Ala Pro
             100                 105                 110

Phe Asn Arg Thr His Arg Ser Lys Arg Ser Ser Ser His Pro Ile Phe
         115                 120                 125
```

His Arg Gly Glu Phe Ser Val Cys Asp Ser Val Ser Val Trp Val Gly
130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr His Thr Phe Val
        195                 200                 205

Lys Ala Leu Thr Met Asp Gly Lys Gln Ala Ala Trp Arg Phe Ile Arg
210                 215                 220

Ile Asp Thr Ala Cys Val Cys Val Leu Ser Arg Lys Ala Val Arg Arg
225                 230                 235                 240

Ala

<210> SEQ ID NO 5
<211> LENGTH: 241
<212> TYPE: PRT
<213> ORGANISM: Homo sapiens

<400> SEQUENCE: 5

Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
                20                  25                  30

Pro Gln Val His Trp Thr Lys Leu Gln His Ser Leu Asp Thr Ala Leu
            35                  40                  45

Arg Arg Ala Arg Ser Ala Pro Ala Ala Ala Ile Ala Ala Arg Val Ala
        50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr His Thr Phe Val
        195                 200                 205

Lys Ala Leu Thr Met Asp Gly Lys Gln Ala Ala Trp Arg Phe Ile Arg
210                 215                 220

Ile Asp Thr Ala Cys Val Cys Val Leu Ser Arg Lys Ala Val Arg Arg
225                 230                 235                 240

Ala

<210> SEQ ID NO 6
<211> LENGTH: 227
<212> TYPE: DNA
<213> ORGANISM: Salmo salar

<400> SEQUENCE: 6
cagttgaagt cggaagttta catacactta agttggagtc attaaaactc gttttcaac      60 tactccacaa atttcttgtt aacaaacaat agttttggca agtcagttag gacatctact    120
ttgtgcatga cacaagtcat ttttccaaca attgtttaca gacagattat ttcacttata    180
attcactgta tcacaattcc agtgggtcag aagtttacat acactaa                  227

<210> SEQ ID NO 7
<211> LENGTH: 340
<212> TYPE: PRT
<213> ORGANISM: Salmo salar

<400> SEQUENCE: 7

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys

```
                290                 295                 300
Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

<210> SEQ ID NO 8
<211> LENGTH: 340
<212> TYPE: PRT
<213> ORGANISM: Salmo salar

<400> SEQUENCE: 8

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
                20                  25                  30

Lys Val Pro Arg Ser Ser Val Gln Thr Ile Val Arg Lys Tyr Lys His
                35                  40                  45

His Gly Thr Thr Gln Pro Ser Tyr Arg Ser Gly Arg Arg Arg Val Leu
50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
                100                 105                 110

Lys Gly Arg Ser Ala Arg Lys Lys Pro Leu Leu Gln Asn Arg His Lys
                115                 120                 125

Lys Ala Arg Leu Arg Phe Ala Thr Ala His Gly Asp Lys Asp Arg Thr
130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
                180                 185                 190

Met Leu Trp Gly Cys Phe Ala Ala Gly Gly Thr Gly Ala Leu His Lys
                195                 200                 205

Ile Asp Gly Ile Met Arg Lys Glu Asn Tyr Val Asp Ile Leu Lys Gln
210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
                260                 265                 270

Pro Asp Leu Asn Pro Ile Glu Asn Leu Trp Ala Glu Leu Lys Lys Arg
                275                 280                 285

Val Arg Ala Arg Arg Pro Thr Asn Leu Thr Gln Leu His Gln Leu Cys
                290                 295                 300

Gln Glu Glu Trp Ala Lys Ile His Pro Thr Tyr Cys Gly Lys Leu Val
305                 310                 315                 320
```

```
Glu Gly Tyr Pro Lys Arg Leu Thr Gln Val Lys Gln Phe Lys Gly Asn
            325                 330                 335

Ala Thr Lys Tyr
            340

<210> SEQ ID NO 9
<211> LENGTH: 340
<212> TYPE: PRT
<213> ORGANISM: Salmo salar

<400> SEQUENCE: 9

Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Arg Val Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
            115                 120                 125

Lys Ala Arg Leu Arg Phe Ala Thr Ala His Gly Asp Lys Asp Arg Thr
        130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Ala Asn Asn Tyr Val Asp Ile Leu Lys Gln
        210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
        290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Lys Gln Phe Lys Gly Asn
            325                 330                 335

Ala Thr Lys Tyr
            340
```

```
<210> SEQ ID NO 10
<211> LENGTH: 340
<212> TYPE: PRT
<213> ORGANISM: Salmo salar

<400> SEQUENCE: 10

Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Gly Glu Ala Cys
                165                 170                 175

Lys Pro Lys Asn Thr Ile Pro Thr Val Lys His Gly Gly Ser Ile
            180                 185                 190

Met Leu Trp Gly Cys Phe Ala Ala Gly Thr Gly Ala Leu His Lys
        195                 200                 205

Ile Asp Gly Ile Met Asp Ala Asn Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

<210> SEQ ID NO 11
<211> LENGTH: 31
<212> TYPE: DNA
```

```
<213> ORGANISM: Homo sapiens

<400> SEQUENCE: 11
ggtgaattcg ggctggaccc tgaacagcgc g                             31

<210> SEQ ID NO 12
<211> LENGTH: 40
<212> TYPE: DNA
<213> ORGANISM: Homo sapiens

<400> SEQUENCE: 12
tatactcgag caggaatggc tgactctgca taaattggcc                    40

<210> SEQ ID NO 13
<211> LENGTH: 37
<212> TYPE: DNA
<213> ORGANISM: Homo sapiens

<400> SEQUENCE: 13
tataggatcc gccaccatga aatgcagctg ggttatc                       37

<210> SEQ ID NO 14
<211> LENGTH: 31
<212> TYPE: DNA
<213> ORGANISM: Homo sapiens

<400> SEQUENCE: 14
gggtccagcc cgaattcacc cctgtagaaa g                             31

<210> SEQ ID NO 15
<211> LENGTH: 30
<212> TYPE: DNA
<213> ORGANISM: Homo sapiens

<400> SEQUENCE: 15
tataggatcc ctctgaggga cccagaaact                               30

<210> SEQ ID NO 16
<211> LENGTH: 29
<212> TYPE: DNA
<213> ORGANISM: Homo sapiens

<400> SEQUENCE: 16
tatactcgag caggtcaggc tcttctcac                                29
```

CELL LINES AND THEIR USE IN ENCAPSULATED CELL BIODELIVERY

CROSS-REFERENCE TO RELATED APPLICATIONS

This application is a continuation application of U.S. Ser. No. 15/851,741 filed Dec. 22, 2017 issued as U.S. Pat. No. 10,888,526 on Jan. 12, 2021, which is a continuation application of U.S. Ser. No. 14/821,498 filed Aug. 7, 2015 issued as U.S. Pat. No. 9,884,023 on Feb. 6, 2018, which is a continuation of U.S. Ser. No. 14/289,856 filed May 29, 2014 issued as U.S. Pat. No. 9,121,037 on Sep. 1, 2015, which is a continuation of U.S. Ser. No. 13/145,669 filed on Oct. 17, 2011 issued as U.S. Pat. No. 8,741,340 on Jun. 3, 2014, which is the U.S. National Stage filing under 35 U.S.C. § 371 of International Application No. PCT/DK2010/050013 filed Jan. 21, 2010, which claims the benefit of U.S. Provisional Application 61/146,754 filed Jan. 23, 2009. U.S. Provisional Application 61/244,993 filed Sep. 23, 2009. Denmark Patent Application No. DK PA 2009 70121 filed Sep. 22, 2009 and Denmark Patent Application No. DK PA 2009 00103 filed Jan. 23, 2009.

FIELD OF INVENTION

The present invention relates to generation of cell lines expressing recombinant proteins for use in naked and encapsulated cell biodelivery of secreted therapeutic molecules. In one embodiment the cell line is human.

BACKGROUND OF INVENTION

Typical methods for introducing DNA into a cell include DNA condensing reagents, lipid-containing reagents as well as virus-mediated strategies. However, these methods have their limitations. For example, there are size constraints associated with DNA condensing reagents and virus-mediated strategies. Further, the amount of nucleic acid that can be transfected into a cell is limited in virus-strategies. Moreover, virus-mediated strategies can be cell-type or tissue-type specific and the use of virus-mediated strategies can create immunologic problems when used in vivo.

One suitable method of overcoming these problems is transposons. Transposons or transposable elements are sequences of DNA that can move around and integrate at different positions within the genome of a single cell, a process called transposition. Transposons include a short nucleic acid sequence with inverted repeat sequences upstream and downstream thereof. Active transposons encode enzymes called transposases that facilitate the excision and insertion of the nucleic acid into the target DNA sequence. Transposon integration into chromosomes provides the basis for long term, or possibly permanent, transgene expression in transgenic cells and organisms.

The transposon system has a wide genetic application span. The transposon system has so far been explored for in vivo protein production in insect larvae where the transposon plasmids are injected directly into the insect pre-blastoderm embryos (WO 2001/29204), The protein of interest can then be purified from the developing larvae or adult insect.

The transposon system has also been utilized to genetically modify stem cells. WO 2009/050657 relates to a method of producing genetically modified stem cells using the transposon-transposase system. The transgenes expressed in the stem cells are marker genes, such as GFP under the control of promoters that are constitutive both in stem cells and differentiated cells. In WO 2009/071334 a method of generating knockout or transgenic animal models using spermatogonial stem cells modified by the transposon system is described.

Thus, it is well know in the state of the art that transposons can be used to generate transgenic cell lines either creating knockout or transgenic cells lines, hence changing the properties of the cells. Due to the fact that transposons integrate into chromosomes long term, or possibly permanent, transgene expression is achieved in transgenic cells and organisms.

In cell based therapies where stable human transgenic cell lines are created for subsequent implantation into a subject as either encapsulated or naked cells there is a need for stable high expression of the transgene following implantation, e.g. under conditions where selection markers cannot be used. Typically, transplanted cells and implanted encapsulated cells must be able to express the transgene for a year or more without any down-regulation such as the down-regulation caused by gene silencing. Traditional expression increasing tools such as codon optimisation, the use of expression enhancing sequences or the use of strong promoters have their limits and may produce variable results.

In this invention the properties of the transposon system is utilized in the generation of a capsule for implantation containing a cell line altered using the transposon system to be secreting a biologically active compound or a polypeptide or an siRNA contributing to the generation of said biologically active peptide. The outer membrane of the capsule is biocompatible and the capsule contains a support matrix for the cells.

SUMMARY OF INVENTION

Thus in a first aspect the invention relates to a capsule for delivery of a secreted biologically active compound to a subject. The capsule comprises
 a. a biocompatible outer membrane and an inner core,
 b. said inner core comprising cells,
 c. said cells comprising a heterologous expression construct comprising a structural gene either coding for a secreted biologically active polypeptide or,
  i. coding for a polypeptide or an siRNA contributing to the generation in the cells of a biologically active secreted compound,
 d. said gene being located between two inverted repeats which are substrates for a transposase or other integrases.

This capsule makes stable high expression of the transgene following implantation possible and the utilization of the transposon system increases the transgene expression several fold compared to traditional transfection of cells.

In another aspect, the invention relates to the use of the capsule of the invention for therapy. As the capsules of the invention produce the biologically active compound stably and at higher levels and in the absence of selection pressure, they are especially adapted for use in therapy. Due to the higher expression levels the number and/or size of the capsules can be reduced.

In another aspect the invention relates to a cell line comprising a heterologous expression construct coding for a structural gene either
 i. coding for a secreted biologically active polypeptide or
 ii. coding for a polypeptide or an siRNA contributing to the generation in the cells of a biologically active secreted compound;

said gene being located between two inverted repeats which are substrates for a transposase.

By generating the cell line using the transposon system an increase in secreted polypeptide is observed even at low copy numbers. A highly efficient and unexpectedly stable transgene expression is hence achieved in the absence of selection pressure. By using a cell line it is ensured that all cells in the composition are identical.

In another aspect the invention relates to a method for producing a recombinant protein comprising culturing the cells according to the invention and recovering said recombinant protein.

Typically in recombinant expression a selection pressure is maintained at least during expansion of the cells to ensure that the cells do not lose the transgene. As the cell lines of the invention can express the transgene stably and at high levels without selection pressure, the use of selection pressure during recombinant manufacturing, e.g. the use of antibiotics, can be avoided. Thereby subsequent down stream processing is facilitated.

In a further aspect the invention relates to a method of generating a cell line capable of secreting a biologically active compound, said method comprising
  a. Transfecting cells with a first and a second expression construct;
  b. Said first expression construct comprising an open reading frame coding for a transposase;
  c. Said second expression construct coding for a secreted biologically active polypeptide or coding for a polypeptide or an siRNA contributing to the generation in the cells of a biologically active secreted compound;
  d. Said second expression construct being located between two inverted repeats which are substrates for said transposase;
  e. Causing transient expression of said transposase, thereby causing integration of said second expression construct into the genome of said human cells.

By using the transposon system for generating a cell line for secretion of a polypeptide a higher yield of secreted polypeptide is achieved. By using the transposon system there is less need for continuous selection pressure as the transgenic cells tend not to lose the expression.

DETAILED DESCRIPTION OF THE INVENTION

Definitions

Figure 1A:
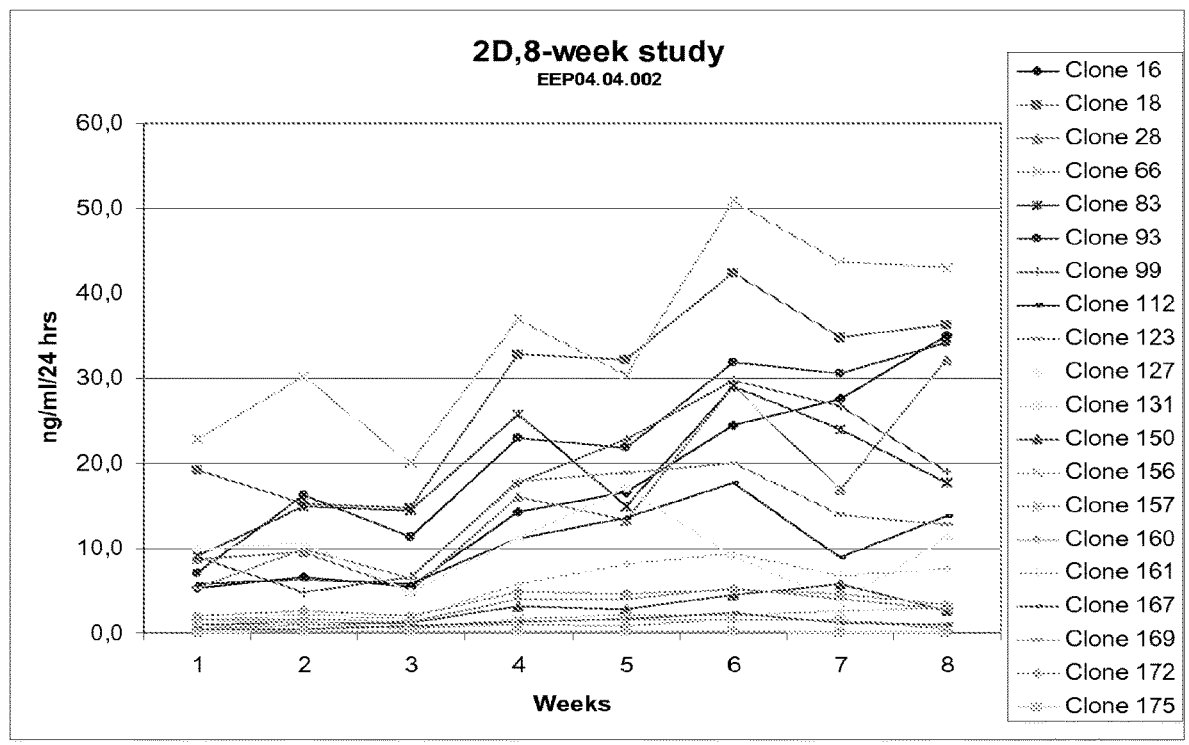
FIG. 1A: 2D, 8 week study, Galanin clones. In vitro stable galanin secreting ARPE-19 clones based on the pCA expression vector. The clones were generated using standard transfection techniques and G418 selection. Clones were cultured without passaging for 8 weeks. Galanin secretion was measured by ELISA.
Figure 1B:
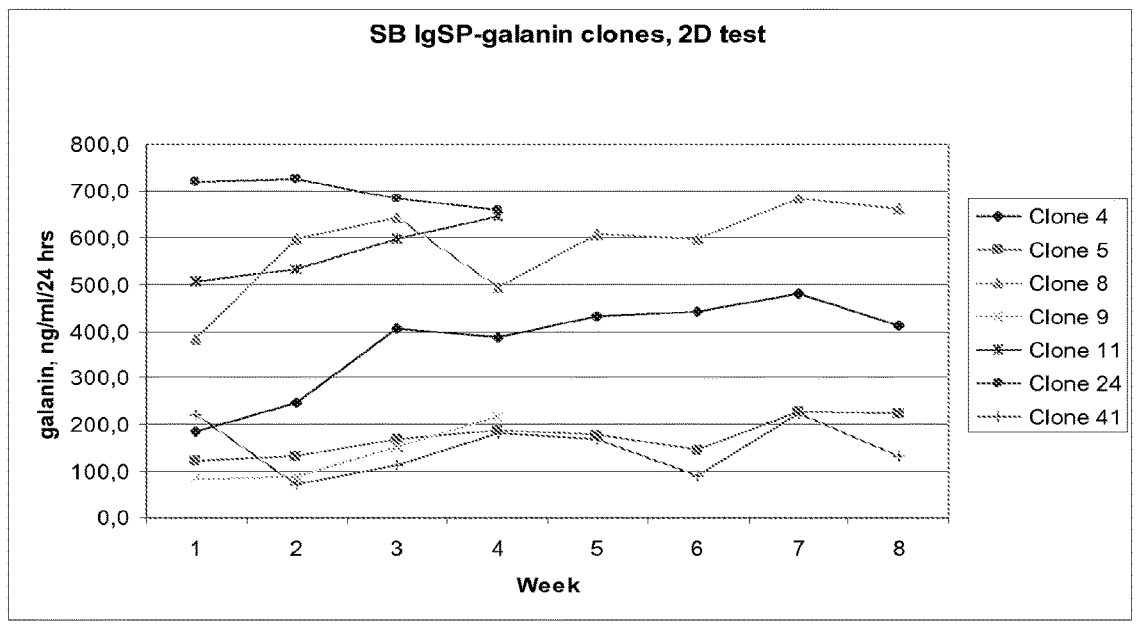
FIG. 1B: 2D, 8 week study, SB IgSP-galanin clones. In vitro stable galanin secreting ARPE-19 clones based on the SB substrate vector pT2. The clones were generated using the SB technology. Clones were cultured without passaging for up to 8 weeks. Galanin secretion was measured by ELISA.
Figure 1C:
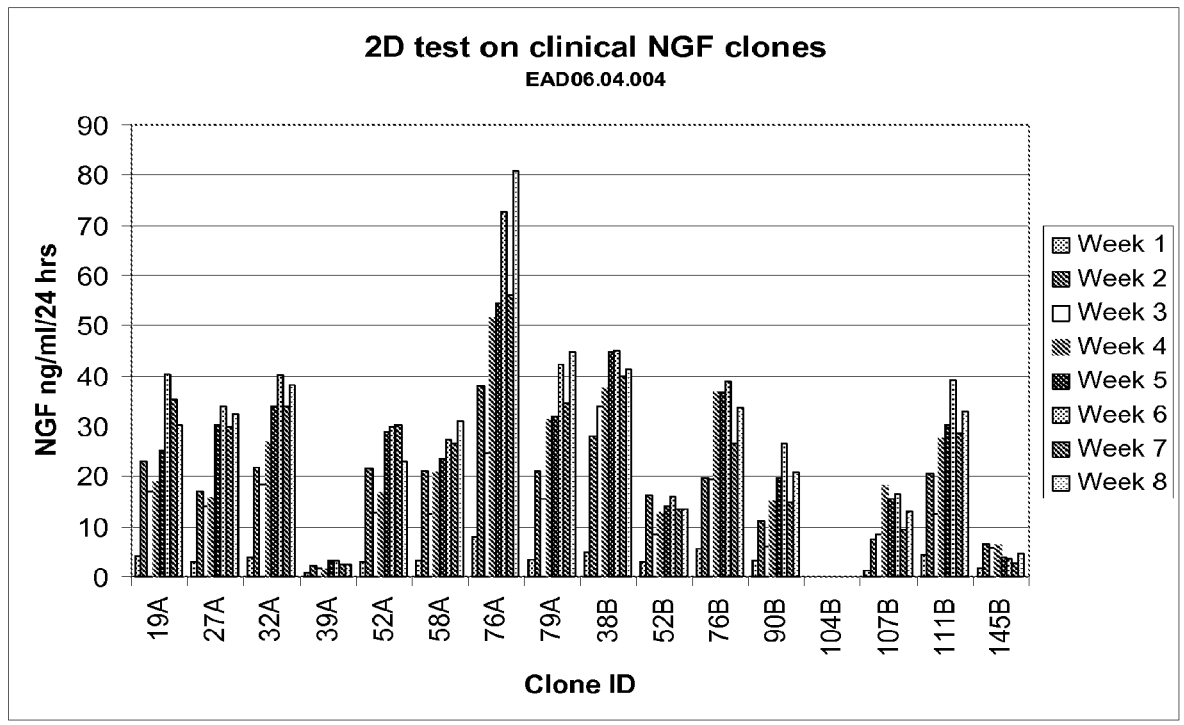
FIG. 1C: 2D test on clinical NGF clones. In vitro stable NGF secreting ARPE-19 clones based on the pCA expression vector. The clones were generated using standard transfection techniques and G418 selection. Clones were cultured without passaging for 8 weeks. NGF secretion was measured by ELISA.
Figure 1D:
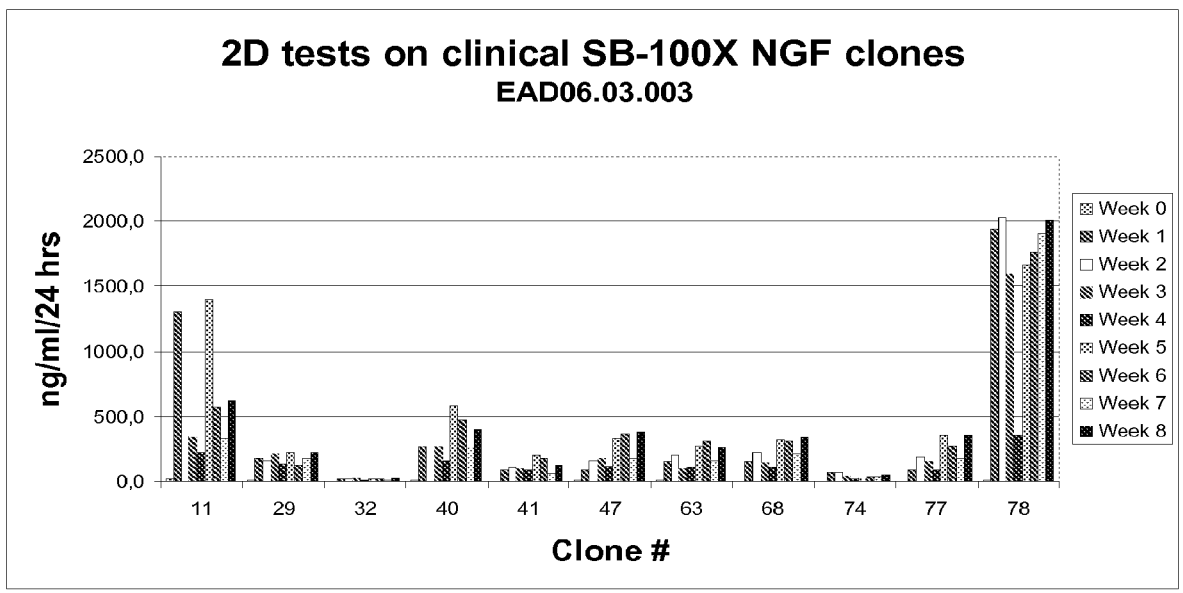
FIG. 1D: 2D test on clinical SB-NGF clones. In vitro stable NGF secreting ARPE-19 clones based on the SB substrate vector pT2. The clones were generated using the SB technology. Clones were cultured without passaging for 8 weeks. NGF secretion was measured by ELISA.

Biological activity refers to the biologically useful effects of a molecule on a specific cell. As used herein "a biologically active compound" is one which is released or secreted from the cell in which it is made and exerts its effect on a separate target cell.

As used herein "a biocompatible capsule" means that the capsule, upon implantation in a host mammal, does not elicit a detrimental host response sufficient to result in the rejection of the capsule or to render it inoperable, for example through degradation.

As used herein, the term "biological agent" refers to any agent, such as a virus, protein, peptide, amino acid, lipid, carbohydrate, nucleic acid, nucleotide, drug, pro-drug or other substance made by a cell that may have an effect on cells whether such effect is harmful, beneficial, or otherwise.

As used herein, a "coding sequence" is a polynucleotide sequence which is transcribed and translated into a polypeptide.

As used herein, the term "Control sequence" refers to polynucleotide sequences which are necessary to effect the expression of coding and non-coding sequences to which they are ligated. Control sequences generally include promoter, ribosomal binding site, and transcription termination sequence. In addition, "control sequences" refers to sequences which control the processing of the peptide encoded within the coding sequence; these can include, but are not limited to sequences controlling secretion, protease cleavage, and glycosylation of the peptide. The term "control sequences" is intended to include, at a minimum, components whose presence can influence expression, and can also include additional components whose presence is advantageous, for example, leader sequences and fusion partner sequences.

"Down regulation" of a promoter means the reduction in the expression of the product of transgene to a level, which may lead to a lack of significant biological activity of the transgene product after in vivo implantation. As used herein "a promoter not subject to down regulation" means a promoter, which, after in vivo implantation in a mammalian host, drives or continues to drive the expression of transgene at a level which is biologically active.

As used herein, the term "expression vectors" refers to vectors that are capable of directing the expression of genes to which they are operatively-linked. In general, expression vectors of utility in recombinant DNA techniques are often in the form of plasmids.

As used herein, the terms "genetic modification" and "genetic engineering" refer to the stable or transient alteration of the genotype of a cell by intentional introduction of exogenous DNA. DNA may be synthetic, or naturally derived, and may contain genes, portions of genes, or other useful DNA sequences. The term "genetic modification" not meant to include naturally occurring alterations such as that which occurs through natural viral activity, natural genetic recombination, or the like.

As used herein "an immunoisolatory capsule" means that the capsule upon implantation into a mammalian host minimizes the deleterious effects of the host's immune system on the cells within its core.

As used herein "long-term, stable expression of a biologically active compound" means the continued production of a biologically active compound at a level sufficient to maintain its useful biological activity for periods greater than one month, preferably greater than three months and most preferably greater than six months.

By a "mammalian promoter" is intended a promoter capable of functioning m a mammalian cell.

As used herein, the term "neurological agents" refers to biological agents that are beneficial to neural cells, a term which encompasses any biologically or pharmaceutically active substance that may prove potentially useful for the survival, proliferation, differentiation or functioning of CNS or eye cells or treatment of neurological or opthalmological diseases or disorders.

A "neuropeptide" is a member of a class of protein-like molecules made in the brain. Neuropeptides consist of short chains of amino acids, with some functioning as neurotransmitters and some functioning as hormones. By short chains are meant peptides with a molecular weight of <5 kD.

As used herein, the term "operatively-linked" is intended to mean that the nucleotide sequence of interest is linked to the regulatory sequence(s) within a recombinant expression vector, in a manner that allows for expression of the nucleotide sequence (e.g., in an in vitro transcription/translation system or in a host cell when the vector is introduced into the host cell).

As used herein, the term "regulatory sequence" is intended to include promoters, enhancers and other expression control elements (e.g., polyadenylation signals).

"Sequence identity": A high level of sequence identity indicates likelihood that the first sequence is derived from the second sequence. Amino acid sequence identity requires identical amino acid sequences between two aligned sequences. Thus, a candidate sequence sharing 70% amino acid identity with a reference sequence, requires that, following alignment, 70% of the amino acids in the candidate sequence are identical to the corresponding amino acids in the reference sequence. Identity may be determined by aid of computer analysis, such as, without limitations, the ClustalW computer alignment program (Higgins D., Thompson J., Gibson T., Thompson J. D., Higgins D. G., Gibson T. J., 1994.

CLUSTAL W: improving the sensitivity of progressive multiple sequence alignment through sequence weighting, position-specific gap penalties and weight matrix choice. Nucleic Acids Res. 22:4673-4680), and the default parameters suggested therein. The ClustalW software is available from as a ClustalW WWW Service at the European Bioinformatics Institute http://www.ebi.ac.uk/clustalw. Using this program with its default settings, the mature (bioactive) part of a query and a reference polypeptide are aligned. The number of fully conserved residues are counted and divided by the length of the reference polypeptide.

The ClustalW algorithm may similarly be used to align nucleotide sequences. Sequence identities may be calculated in a similar way as indicated for amino acid sequences.

As used herein, the term "Transformation" refers to the insertion of an exogenous polynucleotide (i.e., a "transgene") into a host cell. The exogenous polynucleotide is integrated within the host genome.

"Treatment" can be performed in several different ways, including curative, ameliorating and as prophylaxis. Curative treatment generally aims at curing a clinical condition, such as a disease or an infection, which is already present in the treated individual. Ameliorating treatment generally means treating in order to improve, in an individual, an existing clinical condition. Prophylactic treatment generally aims at preventing a clinical condition.

As used herein the term "siRNA" refers to a class of compounds known as "Small interfering RNA", sometimes known as short interfering RNA or silencing RNA. The RNAs being 20-25 nucleotides in length play a variety of roles in biology. Most notably, siRNA is involved in the RNA interference (RNAi) pathway, where it interferes with the expression of a specific gene. An siRNA is generated to be complementary to a part of the transcript of a gene to be silenced. The siRNA is expressed in the target cell using methods described herein. The expressed short siRNA hybridise to the complementary RNA sequence in the target transcript and the resulting double-stranded RNA is degraded by the cell's own machinery. The end result is a down-regulation of the expression of the targeted gene.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein an "inverted repeat" (or IR) is a sequence of nucleotides that is the reversed complement of another sequence further downstream. Inverted repeats define the boundaries in transposons. Inverted repeats may also be called "inverted terminal repeats" or "terminal inverted repeats", as they are located in inverted form at opposite ends of some transposons.

Transposons

At present, two classes of transposons are known, i.e. class I and class II transposons. Class I mobile genetic elements, or retrotransposons, copy themselves by first being transcribed to RNA, then reverse transcribed back to DNA by reverse transcriptase, and then being inserted at another position in the genome. Class II mobile genetic elements, also called DNA-only transposons, move by a cut and paste mechanism, directly from one position to another using the transposase enzyme. Different types of transposases may work in different ways. Some can bind to any part of the DNA molecule, and the target site can be located at any position, while others bind to specific sequences. The transposase then cuts the target site to produce sticky ends, release the transposon and ligates it into the target site. The insertion sites of DNA transposons may be identified by short direct repeats (DR), which are staggered cuts in the target DNA filled by DNA polymerase, followed by inverted repeats (IR), which are important for the transposon excision by transposase.

Both invertebrate and vertebrate transposons hold potential for transgenesis and insertional mutagenesis in model organisms.

In vertebrates, three active transposons are currently known and used: the Tol2 element (Kawakami, K., (2007), Genome Biology, 8 (Suppl 1): S7) and the reconstructed transposons Sleeping Beauty (SB) (Ivies, Z. et al. (2004), Curr. Issues Mol. Biol., 6: 43-56) and Frog Prince (FP) (Miskey, C. et al. (2003), Nucleic Acid Research, 31(24): 6873-6881). Another interesting transposon system in vertebrates the PiggyBac transposon system (Wilson, M. H. et al. (2007), Molecular Therapy, 15(1): 139-145.

The Tol2 transposon isolated from the medaka fish (*Otyzias latipes*) is an autonomous transposon that encodes a fully functional transposase. DNA inserts of fairly large sizes (as large as 11 kilobases) can be cloned into the Toll transposon without reducing transpositional activity. The Tol2 transposon system has been shown to be active in all vertebrate cells tested thus far, including zebrafish, *Xenopus*, chicken, mouse and human. The DNA sequence of the Tol2 transposon is similar to transposons of the hAT family, including hobo from *Drosophila*, Ac from maize and Tam3 from snapdragon (Kawakami, K. (2007), Genome Biology, 8 (suppl 1): S7).

Sleeping Beauty (SB) is a member of the Tel/mariner-like family of transposons and transposases resurrected from the fish genome and exhibits high transpositional activity in a variety of vertebrate cultured cell lines, embryonic stem cells and in both somatic and germ line cells of the mouse in vivo. Sleeping Beauty has already proved to be a valuable tool for functional genomics in several vertebrate model organisms and shows promise for human gene therapeutic applications (Ivies, Z. and Izsvak, Z. (2006), Curr. Gene Ther., 6: 593-607).

The SB transposase and transposon is described in U.S. Pat. Nos. 7,148,203 and 6,489,458. Hyperactive variants of the SB transposase is described in WO 2009/003671, resulting in an improvement of the already valuable SB system as a method for introducing DNA into a cell.

Frog Prince is also a member of the Tc I/marine-like family and has recently been reactivated from genomic transposon copies of the Northern Leopard Frog (*Rana pipiens*). Frog Prince has only approximately 50% sequence similarity to Sleeping Beauty and catalyzes efficient cut and paste transposition in fish, amphibian and mammalian cell lines (Miskey, C. et al., (2003), Nucleic Acids Research, 31(24): 6873-6881).

The PiggyBac transposon system is derived from the cabbage looper moth (*Trichoplusia ni*) and is capable of delivering large transposable elements (as large as 14 kilobases) without a significant reduction in efficiency, The PiggyBac transposon system has been used for transgenesis of insects and for germline mutagenesis in mice (Wilson, M. H. et al., (2007), Molecular Therapy, 15(1): 139-145).

Further transposons that can be used in conjunction Oc31 (see e.g. Calos, Curr Gene Ther. 2006 December; 6(6):633-45), Minos (see e.g. Zagoraiou et al, Proc Natl Acad Sci US A. 2001 Sep. 25; 98(20):11474-8. Epub 2001 Sep. 18), Mariner transposases such as Minos (see e.g. Pavlopoulos et al, Genome Biol. 2007; 8 Suppl 1:S2), and Hermes (e.g. Evertts et al, Genetics. 2007 December; 177(4):2519-23. Epub 2007 Oct. 18).

The abovementioned transposons, do not interact and thus may be used as a genetic tool in the presence of others, which considerably broadens the utility of these elements. Any preferences for different insertion sites can be exploited in a complementary fashion. The DNA transposons have been developed as gene transfer vectors in both invertebrate and vertebrate model organisms. The DNA transposons are strong rivals of the retroviral systems in human gene therapy. For genetic analysis and therapeutic purposes the class 11 transposable elements are the most useful due to their easy laboratory handling and controllable nature.

The transposon system has a wide genetic application span. The transposon system has so far been explored for in vivo protein production in insect larvae where the transposon plasmids are injected directly into the insect pre-blastoderm embryos (WO 2001/29204).

The protein of interest can then be purified from the developing larvae or adult insect. The transposon system has also been utilized to genetically modify stem cells by introduction of transposition to stem cells. WO 2009/050657 relates to a method of producing genetically modified stem cells using the transposon-transposase system. The transgenes expressed in the stem cells are marker genes, such as GFP under the control of promoters that are constitutive both in stem cells and differentiated cells. In WO 2009/071334 a method of generating knockout or transgenic animal models using spermatogonial stem cells modified by the transposon system is described.

In a preferred embodiment of the present invention the nucleic acid coding for the polypeptide contributing to the generation in the cells of a biologically active secreted compound has been inserted into the chromosome by use of a Sleeping Beauty (SB) transposase. More preferably the SB transposase is a hyperactive transposase as described in WO 2009/003671. Hyperactive transposases include Sleeping Beauty variants is selected from variants of SB1OX comprising the amino acid sequence differing from SEQ ID NO 7 by 1 to 20 amino acids including at least one of the following mutations or groups of mutations selected from the group consisting of:

K14R;
K13D;
K13A;
K3OR;
K33A;
T83A;
I100L;
R115H;
R143L;
R147E;
A205K/H207V/K208R/D210E;
H207V/K208R/D210E;
R214D/K215A/E216V/N217Q;
M243H;
M243Q;
E267D;
T314N; and
G317E.

Specifically, preferred SB variants comprise at least the following combination of mutations:
Variant 1: K14R//R214D/K215A/E216V/N217Q;
Variant 2: K33A/R115H//R214D/K215A/E216V/N217Q//M243H;
Variant 3: K14R/K30R//A205K/H207V/K208R/D210E//R214D/K215A/E216V/N217Q//M243H;
Variant 4: K13D/K33A/T83A//H207V/K208R/D210E//M243Q;
Variant 5: K13A/K33N/R214D/K215A/E216V/N217O;

Variant 6: K33A/T83A//R214D/K215A/E216V/N217Q//G317E;
Variant 8: K14R/T83A/1100L/M2430;
Variant 9: K14R/T83A/R143L/M243Q;
Variant 10: K14R/T83A/R147E/M243Q;
Variant 11: K14R/T83A/M243Q/E267D;
Variant 12: K14R/T83A/M243Q/T314N;
Variant 13: K14R/K30R/1 10017/A205K/H207V/K208R/D210EHR214D/K215A/E216V/N217Q11 M243 H;
Variant 14: K14R/K3OR/R1431J/A205K/H207V/K208R/D210E//R214D/K215A/E216V/N217 Q//M24
Variant 15: K14R/K3OR/R147E//A205K/H207V/K208R/D210E//R214D/K215A/E216V/N217QH M243H;
Variant 16: K14R/K30R/A205K/H207V/K208R/D210E//R214D/K215A/E216V/N217Q//M243H/E26 7D;
Variant 17: K14R/K30 R/A205K/H207V/K208 R/D210 E//R214 D/K215A/E216V/N217Q//M243 H/T314 N;
Variant 18: K14R/K3OR//A205K/H207V/K208R/D210E//R214D/K215A/E216V/N21 7Q//M243H/G3 17E;
Variant 19: K14R/K33A/R1 15H//R214D/K215A/E216V/N217Q//M243H;
Variant 20: K14R/K3OR/R1 47E//A205K/H207V/K208R/D210E//R214D/K21 5A/E216V/N217QHM 24 3H/T314N;
Variant 21: K14R/K3OR/R1431J/A205K/H207V/K208R/D210E//R214D/K215A/E216V/N217QH M24 3H/E267D;
Variant 22: K14R/K3OR/R14317/A205K/H207V/K208R/D210EHR214D/K215A/E216V/N217QH M24 3H/T314N;
Variant 23: K14R/K3OR/R14317/A205K/H207V/K208R/D210EHR214D/K215A/E216V/N21 7QHM24 31/G317E;
Variant 24: K14R/K33A/R1 15H/R143L//R214D/K215A/E216V/N217Q//M243H;
Variant 25: K14R/K33A/R1 15H/R147E//R214D/K215A/E216V/N217Q//M243H;
Variant 26: K14R/K33A/R115H//R214D/K215A/E216V/N217Q//M243H/E267D;
Variant 27: K14R/K33A/R115H//R214D/K215A/E216V/N217Q//M243H/T314N;
Variant 28: K14R/K33A/R1 15H//R214D/K215A/E216V/N217Q//M243H/G317E;
Variant 29: K14R/T83A/M243Q/G317E;
Variant 30: K13A/K33A/T83A//R214D/K215A/E216V/N217Q preferably selected from
Variant 1: K14R/R214D//K215A/E216V/N217Q;
Variant 2: K33A/R115H//R214D/K215A/E216V/N217Q//M243H;
Variant 3: K14R/K30RHA205K/H207V/K208R/D210E//R214D/K215A/E216V/N217QHM243 H,
Variant 4: K13D/K33A/T83A//H207V/K208R/D210E//M243Q;
Variant 5: K13A/K33A//R214D/K215A/E216V/N217O;
Variant 6: K33A/T83A//R214D/K215A/E216V/N217Q//G317E;
Variant 7: K14R/T83A/M243Q;
Variant 8: K14R/T83A/1100L7M243Q;
Variant 9: K14R/T83A/R143L/M243Q;
Variant 10: K14R/T83 A/R147E/M243Q;
Variant 11: K14R/T83A/M243Q/E267D;
Variant 12: K14R/T83A/M243Q/T314N;
Variant 14: K14R/K3OR/R14317/A205K/H207V/K208R/D210EHR214D/K215A/E216/N217QH M243 H;
Variant 15: K14R/K3OR/R147E//A205K/H207V/K208R/D210E//R214D/K215A/E216V/N217QH M24 3H;
Variant 16: K14R/K30RHA205K/H207V/K208R/D210E//R214D/K215A/E216V/N2170//M2431H E26 7D;
Variant 17: K14R/K30RHA205K/H207V/K208R/D210E//R214D/K215A/E216V/N217QHM2 43H/T31 4N;
Variant 18: K14R/K30RHA205K/H207V/K208R/D210E//R214D/K215A/E216V/N217QH-1M243H/031 7E;
Variant 19: K14R/K33A/R1 15H//R214D/K215A/E216V/N217Q//M243H;
Variant 20: K14R/K3OR/R147E//A205K/H207V/K208R/D210E//R214D/K215A/E216V/N217QHM 24 3H/T314N;
Variant 21: K14R/K3OR/R1431J/A205K/H207V/K208R/D210E//R214D/K215A/E216V/N217 QHM24 3H/E267D;
Variant 23: 14R/K3OR/R14317/A205K/H207V/K208R/D210EHR214D/K215A/E216V/N217QHM 24 3 H/G317E;
Variant 24: K14R/K33A/R115H/R143L//R214D/K215A/E216V/N217QHM2431H;
Variant 25: K14R/K33A/R1 15H/R147E//R214D/K215A/E216V/N217Q//M243H;
Variant 26: K14R/K33A/R1 15H//R214D/K215A/E216V/N217Q//M243H/E267D;
Variant 27: K14R/K33A/R115H//R214D/K215A/E216V/N217Q//M243H/T314N;
Variant 28: K14R/K33A/R115H//R214D/K215A/E216V/N217Q//M243H/G317E; more preferably selected from
Variant 2: K33A/R115H//R214D/K215A/E216V/N217Q//M243H;
Variant 3: K14R/K30RHA205K/H207V/K208R/D210E//R214D/K215A/E216V/N217QHM243 H;
Variant 14: K14R/K3OR/R1431J/A205K/H207V/K208R/D210E//R214D/K215A/E216V/N217QH M24 3H;
Variant 15: K14R/K3OR/R147E//A205K/H207V/K208R/D210E//R214D/K215A/E216V/N217QH M24 3H;
Variant 16: K14R/K30RHA205K/H207V/K208R/D210E//R214D/K215A/E216V/N2170//M243H/E26 7D;
Variant 19: K14R/K33A/R115H//R214D/K215A/E216V/N217Q//M2431-H;
Variant 20: K14R/K3OR/R1 47E//A205K/H207V/K208R/D210E//R214D/K215A/E216V/N217QHM 24 3HAT314N;
Variant 21: K14R/K3OR/R143L7/A205K/H207V/K208R/D210EHR214D/K215A/E216V/N217Q HM24 3H/E267D;
Variant 23: K14R/K3OR/R143U/A205K/H207V/K208R/D210E//R214D/K215A/E216V/N217QHM2 4 3H/G317E;
Variant 24: K14R/K33A/R1 15H/R1431//R214D/K215A/E216V/N217Q//M243H;
Variant 25: K14R/K33A/R115H/R147E//R214D/K215A/E216V/N217Q//M243H;
Variant 26: K14R/K33A/R115H//R214D/K215A/E216V/N217Q//M243H/E267D;
Variant 27: K14R/K33A/R115H//R214D/K215A/E216V/N2170//M243H/T314N;

Variant 28: K14R/K33A/R1151-1//R214D/K215A/E216V/N217Q//M2431-H/G317E.

In a most preferred embodiment, the hyperactive SB is variant 27, having the amino acid sequence set forth herein as SEQ ID NO 8.

Encapsulated Cell Therapy

Encapsulated cell biodelivery therapy is based on the concept of isolating cells from the recipient host's immune system by surrounding the cells with a semipermeable biocompatible material before implantation within the host. The invention includes a device in which cells are encapsulated in an immunoisolatory capsule. Cells are immunoisolated from the host by enclosing them within implantable polymeric capsules formed by a microporous membrane. This approach prevents the cell-to-cell contact between host and implanted tissues, eliminating antigen recognition through direct presentation.

The cell capsule, in the following referred to as the capsule, has a membrane which is tailored to control diffusion of molecules, such as growth factor hormones, neurotransmitters, peptides, antibodies and complements, based on their molecular weight (Lysaght et al., 56 J. Cell Biochem. 196 (1996), Colton, 14 Trends Biotechnol. 158 (1996)). Using encapsulation techniques, cells can be transplanted into a host without immune rejection, either with or without use of immunosuppressive drugs.

Useful biocompatible polymer capsules usually contain a core that contains cells, either suspended in a liquid medium or immobilised within an immobilising matrix, and a surrounding or peripheral region of permselective matrix or membrane ("jacket") that does not contain isolated cells, that is biocompatible, and that is sufficient to protect cells in the core from detrimental immunological attack. Encapsulation hinders elements of the immune system from entering the capsule, thereby protecting the encapsulated cells from immune destruction. The semipermeable nature of the capsule membrane also permits the biologically active molecule of interest to easily diffuse from the capsule into the surrounding host tissue and allows nutrients to diffuse easily into the capsule and support the encapsulated cells. The capsule can be made from a biocompatible material. A "biocompatible material" is a material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, and nutrients, while allowing metabolic waste to be removed.

A variety of biocompatible materials are suitable for delivery of growth factors by the composition of the invention. Numerous biocompatible materials are known, having various outer surface morphologies and other mechanical and structural characteristics. Preferably the capsule of this invention will be similar to those described by WO 92/19195 or WO 95/05452, incorporated by reference; or U.S. Pat. Nos. 5,639,275; 5,653,975; 4,892,538; 5,156,844; 5,283,187; or U.S. Pat. No. 5,550,050, incorporated by reference. Such capsules allow for the passage of metabolites, nutrients and therapeutic substances while minimizing the detrimental effects of the host immune system.

Components of the biocompatible material may include a surrounding semipermeable membrane and the internal cell-supporting scaffolding. Preferably, the recombinant cells are seeded onto the scaffolding, which is encapsulated by the permselective membrane. The filamentous cell-supporting scaffold may be made from any biocompatible material selected from the group consisting of acrylic, polyester, polyethylene, polypropylene polyacetonitrile, polyethylene teraphthalate, nylon, polyamides, polyurethanes, polybutester, silk, cotton, chitin, carbon, or biocompatible metals. Also, bonded fibre structures can be used for cell implantation (U.S. Pat. No. 5,512,600, incorporated by reference). Biodegradable polymers include those comprised of poly (lactic acid) PLA, poly(lactic-coglycolic acid) PLGA, and poly(glycolic acid) PGA and their equivalents. Foam scaffolds have been used to provide surfaces onto which transplanted cells may adhere (WO 98/05304, incorporated by reference). Woven mesh tubes have been used as vascular grafts (WO 99/52573, incorporated by reference). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

The jacket preferably has a molecular weight cutoff, defined as that molecular weight, where the membrane (the jacket) will reject 90% of the solutes, of less than 1000 kD, more preferably between 50-700 kD, more preferably between 70-300 kD, more preferably between 70-150 kD, such as between 70 and 130 kD. The molecular weight cutoff should be selected to ensure that the bioactive molecule can escape from the capsule while protecting the encapsulated cells from the immune system of the patient.

The thickness of the jacket typically lies in the range of 2 to 200 microns, more preferably from 50 to 150 microns. The jacket should have a thickness to give the capsule sufficient strength to keep the cells encapsulated and should with this in mind be kept as thin as possible to take up as little space as possible.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Preferably, the surrounding semipermeable membrane is a biocompatible semipermeable hollow fibre membrane.

Such membranes, and methods of making them are disclosed by U.S. Pat. Nos. 5,284,761 and 5,158,881, incorporated by reference. The surrounding semipermeable membrane may be formed from a polyether sulfone hollow fibre, such as those described by U.S. Pat. No. 4,976,859 or U.S. Pat. No. 4,968,733, incorporated by reference. An alternate surrounding semipermeable membrane material is poly (acrylonitrile/covinyl chloride) (Pan-PVC).

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations, which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired. A particularly preferred shape is cylinder-shaped as such a shape is easily produced from hollow fibres which can be produced industrially.

A macrocapsule in the present context is a capsule having a volume of at least 1 pL, such as from 1 to 10 pL.

When macrocapsules are used, preferably at least $10^3$ cells are encapsulated, such as between $10^3$ and $10^8$ cells are encapsulated, most preferably $10^5$ to $10^7$ cells are encapsulated in each device. Of course, the number of cells in each capsule depends on the size of the capsule. As a rule of thumb, in a capsule with foam (described below) the present inventors have found that loading between 10,000 and 100,000 cells per pL of capsule (volume calculated as the internal volume including foam) results in a good filling of the capsule, more preferably from 25,000 to 50,000 cells per pL, more 30 preferably from 30,000 to 40,000 cells per pL. The number of cells to be loaded also depends on the size of the cells.

Dosage may be controlled by varying the dimensions (length, diameter) of the capsule and/or by implanting a fewer or greater number of capsules, preferably between 1 and 10 capsules per patient.

The scaffolding may be coated with extracellular matrix (ECM) molecules. Suitable examples of extracellular matrix molecules include, for example, collagen, laminin, and fibronectin. The surface of the scaffolding may also be modified by treating with plasma irradiation to impart charge to enhance adhesion of cells.

Any suitable method of sealing the capsules may be used, including the use of polymer adhesives or crimping, knotting and heat sealing. In addition, any suitable "dry" sealing method can also be used, as described, e.g., in U.S. Pat. No. 5,653,687, incorporated by reference.

The encapsulated cell devices are implanted according to known techniques. Many implantation sites are contemplated for the devices and methods of this invention. These implantation sites include, but are not limited to, the central nervous system, including the brain, spinal cord (see, U.S. Pat. Nos. 5,106,627, 5,156,844, and 5,554,148, incorporated by reference), and the aqueous and vitreous humors of the eye (see WO 97/34586, incorporated by reference).

The disclosed capsule may include an integral tether that extends from the capsule and which is of a length sufficient to reach at least from the treatment site to the proximity of the insertion site thereby facilitating fixation of the capsule at the insertion site, e.g. to the outer surface of the skull. The insertion site is subsequently covered by skin.

To facilitate removal of the capsule from the tissue, e.g. when the treatment comes to an end, or if the capsule must be replaced, the transition between the capsule and the tether could be smooth and without projections of any kind, or the dimension could be increased from the capsule towards the tether. This, obviously, creates an edge between the two parts but since the relatively small capsule forms the distal end of the therapy system, i.e. the end which is towards the body, ancillary damage may be prevented during removal of the capsule. If the capsule and the tether are tubular with circular cross sectional shapes, the radial size of the capsule may therefore preferably be smaller than the radial size of the tether, and the capsule and tether may preferably be joined coaxially to each other. Preferably the capsule of this invention will be similar in design to those described by WO 2006/122551.

Capsules may be filled by using a syringe or alternatively, automated or semi-automated filling may be used as described in WO2007/048413 (incorporated by reference).

Foam Scaffolds

The foam scaffold may be formed from any suitable material that forms a biocompatible foam with an open cell or macroporous structure with a network of pores. An open-cell foam is a reticulate structure of interconnected pores. The foam scaffold provides a non-biodegradable, stable scaffold material that allows attachment of adherent cells. Among the polymers that are useful in forming the foam scaffolds for the devices of this invention are thermoplastics and thermoplastic elastomers.

Some examples of materials useful in forming suitable foam scaffolds are listed in Table 3.

TABLE 3

| Thermoplastics: | Thermoplastic Elastomers: |
| --- | --- |
| Acrylic | Polyamide |
| Modacrylic | Polyester |
| Polyamide | Polyethylene |
| Polycarbonate | Polypropylene |
| Polyester | Polystyrene |
| Polyethylene | Polyurethane |
| Polypropylene | Polyvinyl Alcohol |
| Polystyrene | Silicone |
| Polysulfone | |
| Polyethersulfone | |
| Polyvinylidene fluoride | |

Thermoplastic foam scaffolds made from polysulfone and polyethersulfone, and thermoplastic elastomer foam scaffolds made from polyurethane and polyvinyl alcohol are preferred.

The foam must have some (but not necessarily all) pores of a size that permits cells to attach to the walls or surfaces within the pores. The pore size, pore density and void volume of the foam scaffold may vary. The pore shape may be circular, elliptical or irregular. Because the pore shape can vary considerably, its dimensions may vary according to the axis being measured. For the purposes of this invention, at least some pores in the foam should have a pore diameter of between 20-500 pm, preferably between 50-150 pm. Preferably the foregoing dimensions represent the mean pore size of the foam. If non-circular, the pore may have variable dimensions, so long as its size is sufficient to permit adherent cells to attach to the walls or surfaces within the pore. In one embodiment, foams are contemplated having some elliptical pores that have a diameter of 20-500 pm along the minor axis and a diameter of up to 1500 pm along the major axis.

In addition to the foregoing cell permissive pores sizes, preferably at least a fraction of the pores in the foam should be less than 10 µm to be cell impermissive but still provide channels for transport of nutrients and biologically active molecules throughout the foam. Pore density of the foam (i.e., the number per volume of pores that can accommodate cells, as described above) can vary between 20-90%, preferably between 50-70%. Similarly, the void volume of the foam may vary between 20-90%, preferably between 30-70%.

The walls or surfaces of the pores may be coated with an extracellular matrix molecule or molecules, or other suitable molecule. This coating can be used to facilitate adherence of the cells to the walls of the pores, to hold cells in a particular phenotype and/or to induce cellular differentiation.

Preferred examples of extracellular matrix molecules (ECM) that can be adhered to the surfaces within the pores of the foams include: collagen, laminin, vitronectin, polyomithine and fibronectin. Other suitable ECM molecules include glycosaminoglycans and proteoglycans; such as chrondroitin sulfate, heparin sulfate, hyaluron, dermatan sulfate, keratin sulfate, heparan sulfate proteoglycan (HSPG) and elastin.

The ECM may be obtained by culturing cells known to deposit ECM, including cells of mesenchymal or astrocyte origin. Schwann cells can be induced to synthesize ECM when treated with ascorbate and cAMP. See, e.g., Baron-Van Evercooren et al., "Schwann Cell Differentiation in vitro: Extracellular Matrix Deposition and Interaction," Dev. Neurosci., 8, pp. 182-96 (1986).

In addition, adhesion peptide fragments, e.g., RGD containing sequences (ArgGlyAsp), YIGSR-containing sequences (TyrlleGlySerArg), as well as IKVAV containing sequences (IleLysValAlaVal), have been found to be useful in promoting cellular attachment. Some ROD-containing molecules are commercially available—e.g., PepTite-2000™ (Telios).

The foam scaffolds of this invention may also be treated with other materials that enhance cellular distribution within the device. For example, the pores of the foam may be filled with a non-permissive hydrogel that inhibits cell proliferation or migration. Such modification can improve attachment of adherent cells to the foam scaffold. Suitable hydrogels include anionic hydrogels (e.g., alginate or carageenan) that may repel cells due to charge. Alternately, "solid" hydrogels (e.g., agarose or polyethylene oxide) may also be used to inhibit cell proliferation by discouraging binding of extracellular matrix molecules secreted by the cells.

Treatment of the foam scaffold with regions of a non-permissive material allows encapsulation of two or more distinct cell populations within the device without having one population overgrow the other. Thus non-permissive materials may be used within the foam scaffold to segregate separate populations of encapsulated cells. The distinct populations of cells may be the same or different cell types, and may produce the same or different biologically active molecules. In one embodiment, one cell population produces a substance that augments the growth and/or survival of the other cell population. In another embodiment, multiple cell types producing multiple biologically active molecules are encapsulated. This provides the recipient with a mixture or "cocktail" of therapeutic substances.

The devices of this invention may be formed according to any suitable method. In one embodiment, the foam scaffold may be pre-formed and inserted into a pre-fabricated jacket, e.g., a hollow fibre membrane, as a discrete component.

Any suitable thermoplastic or thermoplastic elastomer foam scaffold material may be preformed for insertion into a pre-fabricated jacket. In one embodiment we prefer polyvinyl alcohol (PVA) sponges for use as the foam scaffold. Several PVA sponges are commercially available. For example, PVA foam sponges #D-3, 60 pm pore size are suitable (Rippey Corp, Kanebo). Similarly, PVA sponges are commercially available from Ivalon Inc. (San Diego, Cailf.) and Hydrofera (Cleveland, Ohio). PVA sponges are water-insoluble foams formed by the reaction of aerated Poly(vinyl alcohol) solution with formaldehyde vapor as the cross-linker. The hydroxyl groups on the PVA covalently crosslink with the aldehyde groups to form the polymer network. The foams are flexible and elastic when wetted and semi-rigid when dried.

As an alternative, support mesh or yarn may be used as described in U.S. Pat. No. 6,627,422.

The filaments used to form the yarn or mesh internal scaffold are formed of any suitable biocompatible, substantially non-degradable material, Materials useful in forming yarns or woven meshes include any biocompatible polymers that are able to be formed into fibres such as, for example, acrylic, polyester, polyethylene, polypropylene, polyacrylonitrile, polyethylene terephthalate, nylon, polyamides, polyurethanes, polybutester, or natural fibres such as cotton, silk, chitin or carbon. Any suitable thermoplastic polymer, thermoplastic elastomer, or other synthetic or natural material with fibre-forming properties may be inserted into a pre-fabricated hollow fibre membrane or a hollow cylinder formed from a flat membrane sheet. For example, silk, PET or nylon filaments used for suture materials or in the manufacture of vascular grafts are highly conducive to this type of application. In other embodiments, metal ribbon or wire may be used and woven. Each of these filament materials has well-controlled surface and geometric properties, may be mass produced, and have a long history of implant use. In certain embodiments, the filaments may be "texturized" to provide rough surfaces and "hand-holds" onto which cell projections may attach. The filaments may be coated with extracellular matrix molecules or surface-treated (e.g. plasma irradiation or NaOH or KOH etching) to enhance cellular adhesion to the filaments.

In one embodiment, the filaments, preferably organized in a non-random unidirectional orientation, are twisted in bundles to form yarns of varying thickness and void volume. Void volume is defined as the spaces existing between filaments. The void volume in the yarn should vary between 20-95%, but is preferably between 50-95%. The preferred void space between the filaments is between 20-200 pm, sufficient to allow the scaffold to be seeded with cells along the length of the yarn, and to allow the cells to attach to the filaments. The preferred diameter of the filaments comprising the yarn is between 5-100 pm. These filaments should have sufficient mechanical strength to allow twisting into a bundle to comprise a yarn. The filament cross-sectional shape can vary, with circular, rectangular, elliptical, triangular, and star-shaped cross-section being preferred.

In another embodiment, the filaments or yarns are woven into a mesh. The mesh can be produced on a braider using carriers, similar to bobbins, containing monofilaments or multifilaments, which serve to feed either the yarn or filaments into the mesh during weaving. The number of carriers is adjustable and may be wound with the same filaments or a combination of filaments with different compositions and structures. The angle of the braid, defined by the pick count, is controlled by the rotational speed of the carriers and the production speed. In one embodiment, a mandrel is used to produce a hollow tube of mesh. In certain embodiments, the braid is constructed as a single layer, in other embodiments it is a multi-layered structure. The tensile strength of the braid is the linear summation of the tensile strengths of the individual filaments.

Examples of suitable monofilaments for use in the present invention are found in U.S. Pat. No. 6,627,422. One example is a PET yarn which is woven into a braid. This PET braid was constructed from a 34 strand, 44 denier multifilament yarn woven onto a 760 pm O.D. mandrel with a 16 carrier braider at a pick count of 20 picks per inch (ppi). The PET yarn may also be used in non-woven strands. Another example is nylon monofilaments woven into a braid. This nylon braid was constructed from a 13 strand, 40 denier multifilament yarn woven onto a 760 pm O.D. mandrel with a 16 carrier braider at a pick count of 18 ppi. A further example includes stainless steel multifilaments woven into a braid. This stainless steel braid was constructed from a ribbon woven onto a 900 pm O.D. mandrel with a 16 carrier braider at a pick count of 90 ppi. The tensile strength of these PET, nylon, and stainless steel braids was 2.7, 2.4, and 3.6 kg force at break, respectively.

In one embodiment, a tubular braid is constructed. In an additional embodiment, the braid is inserted into a hollow fibre membrane. In a further embodiment, cells are seeded onto the hollow fibre membrane. In an additional embodiment, the cells are allowed to infiltrate the wall of the mesh tube to maximize the surface area available for cell attachment. In this embodiment, the braid serves both as a cell scaffold matrix and as an inner support for the device. The increase in tensile strength for the braid-supported device is significantly higher than in alternative approaches.

Cell Lines

Many different cell types may be encapsulated in the devices according to the present invention. These include well-known, publicly available immortalized cell lines, spontaneously immortalised cell lines as well as dividing primary cell cultures. As cell lines in some embodiments are to be transfected or transduced, clones have to be selected, expanded and cell banked, it is preferable that the cells or cell lines are capable of undergoing a significant number of divisions.

Cell lines with long term propagation potential may be created from a wide variety of cells, including progenitor and/or precursor cells. Also suitable are stem cells including pluripotent and multipotent stem cells, embryonal stem cells, neural stem cells, and hematopoietic stem cells.

Examples of cell lines include Chinese hamster ovary cells (CHO); CHO-KI; baby hamster kidney cells (BHK); mouse fibroblast-3T3 cells; African green monkey cell lines (including COS-1, COS-7, BSC-1, BSC-40, BMT-10 and Vero); rat adrenal pheochromocytoma (PC12 and PC12A); AT3, rat glial tumor (C6); rat neuronal cell line RN33b; rat hippocampal cell line HiB5; growth factor expanded stem cells; EGF-responsive neurospheres; bFGF-responsive neural progenitor stem cells derived from the CNS of mammals [Richards et al., PNAS 89: 8591-8595 (1992); Ray et al., PNAS 90: 3602-3606 (1993)]; foetal cells; primary fibroblasts; Schwann cells; astrocytes; [3-TC cells; Hep-G2 striatal cells; oligodendrocytes and their precursors; mouse myoblast cells-C2Cl2; human glial-derived cells-Hs683; human glial-derived cells-A172; HE1193T; porcine glioblasts; neuronal cells; neurons; astrocytes; interneurons; chondroblasts isolated from human long bone; human embryonic kidney cells HEK293; HeLa; rabbit corneal-derived cells (SIRC); ARPE-19, and CAC cells.

Preferred cell lines for mammalian recombinant production include CHO, CHO-1, HE1193T, HEK293, COS, PC12, HiB5, RN33b, and BHK cells.

The invention also contemplates encapsulation of two or more separately transfected cells or cell lines in the same device, each cell line secreting at least one of the desired molecules. Furthermore, the invention contemplates encapsulation of one cell line transfected with more than one expression construct e. g. two or more expression constructs of the invention. Alternatively, separate devices producing each molecule separately may be implanted.

Many different cell types may be encapsulated in the devices according to the present invention. These include well-known, publicly available immortalized cell lines, spontaneously immortalised cell lines as well as dividing primary cell cultures. As cell lines in some embodiments are to be transfected or transduced, clones have to be selected, expanded and cell banked, it is preferable that the cells or cell lines are capable of undergoing a significant number of divisions.

The choice of cell depends upon the intended application. The cells may naturally produce the desired biologically active molecule or may be genetically engineered to do so.

In a preferred embodiment, the cells are of human origin in order to reduce the risk of immune reaction in a human recipient. Even though the cells are encapsulated behind a semipermeable membrane, a non-human cell line inherently produces non-human proteins and metabolites, which—although secreted at a low level—may trigger an immune response in a human host. In the case of implantation into non-human mammals it is preferable that the cells are of the same species as the mammal into which the capsules are to be implanted.

In the broadest aspect this includes any human cell culture or cell line, whether polyclonal or monoclonal. Monoclonal cell lines are more preferable, as they can be better characterised.

Human cell lines may have been immortalised by insertion of a heterologous immortalisation gene, they may be spontaneously immortal, or they may be growth factor expanded primary cells or stem cells.

For ex vivo gene therapy, the preferred group of cells includes neuronal cells, neuronal precursor cells, neuronal progenitor cells, fibroblast cells, hemapoetic cells, hemapoetic stem cells, stem cells, foetal cells and embryonic stem cells. In one embodiment the cells are not embryonic stem cells.

In a preferred embodiment of the invention, the human cell line has not been immortalised with the insertion of a heterologous immortalisation gene. As the invention relates to cells which are particularly suited for cell transplantation, whether as naked cells or—preferably—as encapsulated cells, such immortalised cell lines are less preferred as there is an inherent risk that they start proliferating in an uncontrolled manner inside the human body and potentially form tumours if they carry known oncogenes.

Preferably, the cell line is capable of phagocytising. Through phagocytosis the cells will be capable of clearing debris shed by decaying or dying cells within the device.

Preferably, the cell line is a contact inhibited cell line or a cell line, which can 10 differentiate inside the capsule, e.g. a stem cell. By a contact inhibited cell line is intended a cell line which when grown in 2-D cultures grows to confluency and then substantially stops dividing. This does not exclude the possibility that a limited number of cells escape the 2D layer. Contact inhibited cells may also be grown in 3D, e.g. inside a capsule. Also inside the capsules, the cells grow to confluency and then significantly slow down proliferation rate or completely stop dividing.

A particularly preferred type of cells include epithelial cells which are by their nature contact inhibited and which form stable monolayers in culture. Even more preferred are retinal pigment epithelial cells (RPE cells). The source of RPE cells is by primary cell 20 isolation from the mammalian retina. Protocols for harvesting RPE cells are well-defined (Li and Turner, 1988, Exp. Eye Res. 47:911-917; Lopez et al., 1989, Invest. Ophthalmol. Vis. Sci. 30:586-588) and considered a routine methodology. In most of the published reports of RPE cell cotransplantation, cells are derived from the rat (Li and Turner, 1988; Lopez et al., 1989). According to the present invention RPE cells are derived from humans. In addition to isolated primary RPE cells, cultured human RPE cell lines may be used in the practice of the invention.

All normal diploid vertebrate cells have a limited capacity to proliferate, a phenomenon that has come to be known as the Hayflick limit or replicative senescence. In human fibroblasts, this limit occurs after 50-80 population doublings, after which the cells remain in a viable but non-dividing senescent state for many months. This contrasts to the behavior of most cancer cells, which have escaped from the controls limiting their proliferative capacity and are effectively immortal.

It is preferable that the cells are capable of undergoing a certain number of cell divisions so they can be genetically modified and expanded to produce enough cells for encapsulated cell therapy or transplantation therapy. Accordingly a preferred cell line is capable of undergoing at least 50 doublings, more preferably at least 60 doublings, more preferably at least 70 doublings, more preferably at least 80 doublings, more preferably at least 90 doublings, such as approximately 100 doublings.

For encapsulation, the cells are preferably able to survive and maintain a secretion of a therapeutic molecule at the low oxygen tension levels of the human body, e.g. within the CNS. Preferably the cell line of the invention is capable of surviving at an oxygen tension below 5%, more preferably below 2%, more preferably below 1%. 1% oxygen tension corresponds to the oxygen level in the brain.

A cell line for an encapsulated cell biodelivery should have as many of the following characteristics as possible: (1) The cells should be hardy under stringent conditions (the encapsulated cells should be functional in the vascular and avascular tissue cavities such as in the central nervous system intraparenchyrnally or within the ventricular or intrathecal fluid spaces or the eye, especially in the intraocular environment). (2) The cells should be able to be genetically modified to express a therapeutic molecule. (3) The cells should be able to go through a relatively high number of divisions and have a relatively long life span (the cells should produce sufficient progenies to be banked, characterised, engineered, safety tested and clinical lot manufactured). (4) The cells must be of human origin (which increases compatibility between the encapsulated cells and the host). (5) The cells should exhibit greater than 80% viability for a period of more than one month in vivo in the device (which ensures long-term delivery). (6) The encapsulated cells should deliver an efficacious quantity of a therapeutic molecule (which ensures effectiveness of the treatment). (7) When encapsulated, the cells should not cause a significant host immune reaction (which ensures the longevity of the graft). (8) The cells should be non-tumourigenic (to provide added safety to the host, in case of device leakage).

In a screening and characterisation of several cell lines it has been found that the ARPE-19 cell line (Dunn et al., 62 Exp. Eye Res. 155-69 (1996), Dunn et al., 39 Invest. Ophthalmol. Vis. Sci. 2744-9 (1998), Finnemann et al., 94 Proc. Natl. Acad. Sci. USA 12932-7 (1997), Randa et al., 66 Exp. Eye. 411-9 (1998), Holtkamp et al., 112 Clin. Exp. Immunol. 34-43 (1998), Maidji et al., 70 J. Virol. 8402-10 (1996)) has all of the characteristics of a successful platform cell for an encapsulated cell-based delivery system (U.S. Pat. No. 6,361,771, Tao et al). The ARPE-19 cell line was superior to the other cell lines tested.

The ARPE-19 cell line is available from the American Type Culture Collection (ATCC Number CRL-2302). The ARPE-19 cell line is derived from cultures of normal retinal pigmented epithelial (RPE) cells and express the retinal pigmentary epithelial cell-specific markers CRALBP and RPE-65. ARPE-19 cells form stable monolayers, which exhibit morphological and functional polarity. ARPE-19 cells may be cultured in Complete Growth Medium, the serum-containing medium recommended by the cell depositor. Complete Growth Medium is either a 1:1 mixture of Dulbecco's modified Eagle's medium and Ham's F12 medium with 3 mM L-glutamine, 90%; foetal bovine serum, 10% or a 1:1 mixture of Dulbecco's modified Eagle's medium and Ham's F12 medium with HEPES buffer containing 10% fetal bovine serum, 56 mM final concentration sodium bicarbonate and 2 mM L-glutamine. The cells are preferably incubated at 37° C. in 5% C02. The cells are typically plated and grown in Falcon tissue culture treated 6 or 12-well plates or T25 or T75 flasks. For subculturing, medium is removed, and the ARPE-19 cells are preferably rinsed with 0.05% trypsin, 0.02% EDTA solution, and the trypsin is removed. One to two ml of additional trypsin solution is added. The culture is incubated at room temperature (or at 37° C.) until the ARPE-19 cells detach. A subcultivation ratio of 1:3 to 1:5 is recommended.

The hardiness of candidate cell lines for encapsulated cell therapy can be tested using the following three-step screen. (a) Cell viability screen (The cells may be evaluated under stressed conditions using artificial aqueous humor (aAH) medium or artificial cerebral spinal fluid (aCSF) medium). (b) In vitro ECM screen (the cells may be evaluated in an in vitro extra-cellular matrix (ECM) screen). (c) In vivo device viability screen (the encapsulated cells may be evaluated in an in vivo membrane screen). A detailed description of the screens and results with several human and non human cell lines are found in U.S. Pat. No. 6,361,771 (incorporated by reference).

In the three types of screens described above, ARPE-19 cells has proven superior to a number of other cell lines tested (see U.S. Pat. No. 6,361,771). In particular it should be noted that BHK cells which have been used in the prior art to secrete NGF did not pass the cell viability screen.

In another embodiment the cell line is selected from the group consisting of: human immortalised fibroblast cell lines, human immortalised mesenchymal stem cell lines, human immortalised astrocyte cell lines, human immortalised mesencephalic cell lines, and human immortalised endothelial cell lines, preferably immortalised with SV40T, vmyc, or the catalytic subunit of telomerase (TERT).

Another type of preferred human cells according to the invention are immortalised human astrocyte cell lines. The method for generating an immortalised human astrocyte cell lines has previously been described (Price T N, Burke J F, Mayne L V. A novel human astrocyte cell line (A735) with astrocyte-specific neurotransmitter function. In Vitro Cell Dev Biol Anim. 1999 May; 35(5):279-88.). This protocol may be used to generate astrocyte cell lines.

The following three modifications of that protocol are preferably made to generate additional human astrocyte cell lines.

Human foetal brain tissue dissected from 5-12 weeks old foetuses may be used instead of 12-16 weeks old tissue.

The immortalisation gene v-myc may be used instead of the SV40 T antigen.

Retroviral gene transfer may be used instead of transfection with plasmids by conventional plasmid transfection techniques (including calcium phosphate precipitation).

Growth factor expanded cell lines have the advantage that they depend on added mitogens for continued proliferation. Therefore upon withdrawal of the mitogen prior to or in connection with the filling of a device with cells, the cells stop proliferating and will not proliferate again after implantation into the human body. Some growth factor expanded cell lines may also differentiate upon withdrawal of the mitogen. Growth factor expanded cell lines include stem cells, such as neural stem cells and embryonal stem cells.

Methods for controlling cell distribution within an encapsulation device have also been discussed. See, e.g., U.S. Pat. No. 5,795,790, herein incorporated by reference. The cells are exposed to a treatment that inhibits cell proliferation, promotes cell differentiation, or affects cell attachment to a growth surface within the bioartificial organ. Such treatments include the steps of (1) genetically manipulating cells, (2) exposing the cells to a proliferation-inhibiting compound or a differentiation-inducing compound or removing the cells from exposure to a proliferation-stimulating compound or a differentiation-inhibiting compound; exposing the cells to irradiation, and (3) modifying a growth surface of the encapsulation device with extracellular matrix molecules, molecules affecting cell proliferation or adhesion, or an inert scaffold, or a combination thereof. These treatments may be used in combination. In a preferred treatment, cells are exposed to and then removed from exposure to a proliferation-stimulating and differentiation inhibiting compound prior to encapsulation of the cells in the semipermeable biocompatible membrane. Upon in vivo implantation of the encapsulation device in a host, cellular proliferation is inhibited and cellular differentiation is promoted.

Long Term Stability

Preferably the cell lines of the present invention are capable of surviving for extended periods (several months and up to one year or more) when transplanted as encapsulated cells in vivo. The cell lines are preferably also capable of maintaining a secretion of bioactive compound at a level sufficient to ensure the therapeutic efficacy for a period greater than one month, preferably greater than three months, more preferably greater than six months. It is also preferable that the cells are capable of maintaining a relevant secretion of bioactive compound after encapsulation for at least one month, more preferably at least three months, more preferably at least six months.

The level of secretion preferably is at least 200 ng biologically active growth factor such as NGF per $10^6$ cells per 24 hours, more preferably at least 225 ng, more preferably at least 250 ng, more preferably at least 275 ng, more preferably at least 300 ng, more preferably at least 325 ng, more preferably at least 350 ng, more preferably at least 375 ng, more preferably at least 400 ng, more preferably at least 425 ng, more preferably at least 450 ng, more preferably at least 500 ng, more preferably 525 ng, more preferably 550 ng, more preferably 575 ng, more preferably 600 ng, more preferably 625 ng, more preferably 650 ng, more preferably 675 ng, more preferably 700 ng, more preferably 725 ng, more preferably 750 ng, more preferably 775 ng, more preferably 800 ng.

The level of secretion preferably is at least 50 ng biologically active neuropeptide such as Galanin per $10^6$ cells per 24 hours, more preferably at least 100 ng, more preferably at least 150 ng, more preferably at least 175 ng, more preferably at least 200 ng, more preferably at least 225 ng, more preferably at least 250 ng, more preferably at least 275 ng, more preferably at least 300 ng, more preferably at least 325 ng, more preferably at least 350 ng, more preferably at least 400 ng, more preferably 425 ng, more preferably 450 ng, more preferably 475 ng, more preferably 500 ng, more preferably 525 ng, more preferably 550 ng, more preferably 575 ng, more preferably 600 ng, more preferably 625 ng, more preferably 650 ng, more preferably 675 ng, more preferably 700 ng, more preferably 725 ng, more preferably 750 ng, more preferably 775 ng, more preferably 800 ng, more preferably 825 ng, more preferably 850 ng, more preferably 875 ng, more preferably 900 ng, more preferably 925 ng, more preferably 950 ng.

When measured on a capsule level, the capsule (comprising encapsulated cells) is preferably capable of secreting in excess of 20 ng biologically active compound per 24 hours. More preferably, the amount of biologically active compound per 24 hours per device is at least 25 ng, more preferably at least 30 ng, more preferably at least 40 ng, more preferably at least 50 ng, more preferably at least 60 ng, more preferably at least 70 ng, more preferably at least 80 ng, more preferably at least 90 ng, more preferably at least 100 ng, more preferably at least 125 ng, more preferably at least 150 ng, more preferably at least 175 ng, more preferably at least 200 ng. These numbers refer to cylindrical devices of 5-7 mm length having an inner diameter of 500-700 i.tm and being loaded with 50000 cells.

Genetic Engineering of Cells for Encapsulation

Cells can be genetically engineered to overexpress a therapeutic molecule. The terms "genetic modification" and "genetic engineering" refer to the stable or transient alteration of the genotype of a cell by intentional introduction of exogenous DNA. DNA may be synthetic, or naturally derived, and may contain genes, portions of genes, or other useful DNA sequences. The term "genetic modification" is not meant to include naturally occurring alterations such as that which occurs through natural viral activity, natural genetic recombination, or the like.

Any useful genetic modification of the cells is within the scope of the invention. For example, cells may be modified to produce or increase production of a biologically active substance such as a neurotransmitter or growth factor or the like. The genetic modification can be performed either by infection with viral vectors (retrovirus, modified herpes viral, herpes-viral, adenovirus, adeno-associated virus, and the like) or transfection using methods known in the art (lipofection, calcium phosphate transfection, DEAE-dextran, electroporation, and the like) (see, Maniatis et al., in Molecular Cloning: A Laboratory Manual (Cold Spring Harbor Laboratory, N.Y., 1982)). For example, the chimeric gene constructs can contain viral, for example retroviral long terminal repeat (LTR), simian virus 40 (SV40), cytomegalovirus (CMV); or mammalian cell-specific promoters. In addition, the vectors can include a drug selection marker, such as the *E. coli* aminoglycoside phosphotransferase gene, which when co-infected with the test gene, confers resistance to geneticin (0418), a protein synthesis inhibitor.

Cells can be genetically modified using transfection with expression vectors. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

In one protocol, vector DNA containing the genes are diluted in 0.1×TE (1 mM Tris pH 8.0, 0.1 mM EDTA) to a concentration of 40 fag/ml. 22 µl of the DNA is added to 250 pl of 2.times.HIBS (280 mM NaCl, 10 mM KCl, 1.5 mM Na2HPO4, 12 mM dextrose, 50 mM HEPES) in a disposable, sterile 5 ml plastic tube. 31 µl of 2 M CaCb is added slowly and the mixture is incubated for 30 minutes (min) at room temperature. During this 30 min incubation, the cells are centrifuged at 800 g for 5 min at 4° C. The cells are re-suspended in 20 volumes of ice-cold PBS and divided into aliquots of $1 \times 10^7$ cells, which are again centrifuged. Each aliquot of cells is resuspended in 1 ml of the DNA-CaCb suspension, and incubated for 20 min at room temperature. The cells are then diluted in growth medium and incubated for 6-24 hr at 37° C. in 5%-7% C02. The cells are again centrifuged, washed in PBS and returned to 10 ml of growth medium for 48 hr.

Suitable vehicles for direct DNA, plasmid polynucleotide, or recombinant vector administration include, without limitation, saline, or sucrose, protamine, polybrene, polylysine, polycations, proteins, calcium phosphate, or spermidine. See e.g, WO 94/01139.

Cells can also be genetically modified using calcium phosphate transfection techniques. For standard calcium phosphate transfection, the cells are mechanically dissociated into a single cell suspension and plated on tissue culture-treated dishes at 50% confluence (50,000-75,000 cells/cm$^2$) and allowed to attach overnight. In one protocol, the modified calcium phosphate transfection procedure is performed as follows: DNA (15-25 pg) in sterile TE buffer (10 mM Tris, 0.25 mM EDTA, pH 7.5) diluted to 440 pl with TE, and 60 µl of 2 M CaCb (pH to 5.8 with 1M HEPES buffer) is added to the DNA/TE buffer.

A total of 500 µl of 2×HeBS (HEPES-Buffered saline; 275 mM NaCl, 10 mM KCl, 1.4 mM Na2HPO4, mM dextrose, 40 mM HEPES buffer powder, pH 6.92) is added dropwise to this mix. The mixture is allowed to stand at room temperature for 20 min. The cells are washed briefly with 1×HeBS and 1 ml of the calcium phosphate precipitated DNA solution is added to each plate, and the cells are incubated at 37° C. for 20 min. Following this incubation, 10 ml of "Complete Medium" is added to the cells, and the plates are placed in an incubator (37° C., 9.5% C02) for an additional 3-6 hours. The DNA and the medium are removed by aspiration at the end of the incubation period. The cells are washed, fresh medium is added and then cells are returned to the incubator.

The calcium phosphate co-precipitation technique can be used, as described in WO 93/06222.

Moreover, cells can be genetically engineered to produce a desired secreted factor.

The desired secreted factor can be encoded by either a synthetic or recombinant expression vector. The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. The term "recombinant" refers to the molecular biological technology for combining polynucleotides to produce useful biological products, and to the polynucleotides and peptides produced by this technology. The polynucleotide can be a recombinant construct (such as a vector or plasmid) which contains the polynucleotide encoding the desired secreted factor operatively-linked to polynucleotides encoding regulatory elements such as promoters, termination signals, and the like. Within a recombinant expression vector, "operatively-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. A control sequence operatively-linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. In addition, "control sequences" refers to sequences which control the processing of the peptide encoded within the coding sequence; these can include, but are not limited to sequences controlling secretion, protease cleavage, and glycosylation of the peptide. The term "control sequences" is intended to include, at a minimum, components whose presence can influence expression, and can also include additional components whose presence is advantageous, for example, leader sequences and fusion partner sequences. A "coding sequence" is a polynucleotide sequence which is transcribed and translated into a polypeptide. Two coding polynucleotides are "operatively-linked" if the linkage results in a continuously translatable sequence without alteration or interruption of the triplet reading frame. A polynucleotide is operatively-linked to a gene expression element if the linkage results in the proper function of that gene expression element to result in expression of the desired secreted factor. "Transformation" is the insertion of an exogenous polynucleotide (i.e., a "transgene") into a host cell. The exogenous polynucleotide is integrated within the host genome. A polynucleotide is "capable of expressing" a desired secreted factor if it contains nucleotide sequences which contain transcriptional and translational regulatory information and such sequences are "operatively-linked" to polynucleotide which encode the desired secreted factor. A polynucleotide that encodes a peptide coding region can then be amplified, for example, by preparation in a bacterial vector, according to conventional methods, for example, described in the standard work Sambrook et al., Molecular Cloning: A Laboratory Manual (Cold Spring Harbor Press 1989). Expression vehicles include plasmids or other vectors.

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many genes consists of the promoter and in some cases enhancer or regulator elements (Banerji et al., Cell 27: 299 (1981); Corden et al., Science 209: 1406 (1980); and Breathnach and Chambon, Ann. Rev. Biochem. 50: 349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res. 11: 1855 (1983); Capecchi et al., In: Enhancer and eukaryotic gene expression, Gulzman and Shenk, eds., pp. 101-102, Cold Spring Harbor Laboratories (NY 1991). Other potent promoters include those derived from cytomegalovirus (CMV) and other wild-type viral promoters and the UbiC promoter derived from human ubiquitin C (WO 98/32869).

Promoter and enhancer regions of a number of non-viral promoters have also been described (Schmidt et al., Nature 314: 285 (1985); Rossi and deCrombrugghe, Proc. Natl. Acad. Sci. USA 84: 5590-5594 (1987)). Methods for maintaining and increasing expression of transgenes in quiescent cells include the use of promoters including collagen type I (1 and 2) (Prockop and Kivirikko, N. Eng. J. Med. 311: 376 (1984); Smith and Niles, Biochem. 19: 1820 (1980); de Wet et al., J. Biol. Chem., 258: 14385 (1983)), SV40 and LTR promoters.

According to one embodiment of the invention, the promoter is a constitutive promoter selected from the group consisting of: chicken beta-actin (CAG), ubiquitin promoter, CMV promoter, JeT promoter (U.S. Pat. No. 6,555,674), SV40 promoter, Mt1 promoter, human UbiC and Elongation Factor 1 alpha promoter (EF-1alpha). A particularly preferred promoter is one which is not subject to down regulation in vivo.

Examples of inducible/repressible promoters include: Tet-On, Tet-Off, Rapamycin-inducible promoter, Mxl, Mo-MLV-LTR, progesterone, RU486.

In addition to using viral and non-viral promoters to drive transgene expression, an enhancer sequence may be used to increase the level of transgene expression. Enhancers can increase the transcriptional activity not only of their native gene but also of some foreign genes (Armelor, Proc. Natl. Acad. Sci. USA 70: 2702 (1973)). For example, in the present invention collagen enhancer sequences may be used with the collagen promoter 2 (I) to increase transgene expression. In addition, the enhancer element found in SV40 viruses may be used to increase transgene expression. This enhancer sequence consists of a 72 base pair repeat as described by Gruss et al., Proc. Natl. Acad. Sci. USA 78: 943 (1981); Benoist and Chambon, Nature 290: 304 (1981), and Fromm and Berg, J. Mol. Appl. Genetics, 1: 457 (1982), all of which are incorporated by reference herein. This repeat sequence can increase the transcription of many different viral and cellular genes when it is present in series with various promoters (Moreau et al., Nucleic Acids Res. 9: 6047 (1981).

Further expression enhancing sequences include but are not limited to Kozak consensus sequence, Woodchuck hepatitis virus post-transcriptional regulation element, WPRE, SP163 enhancer, CMV enhancer, non-translated 5' or 3' regions from the tau, TH or APP genes, and Chicken [beta]-globin insulator or other insulators. Preferable enhancing elements include Kozak consensus sequence, WPRE and beta-globin insulator.

The polynucleotide encoding the desired secreted factor can be prepared by chemical synthesis methods or by recombinant techniques. The polypeptides can be prepared conventionally by chemical synthesis techniques, such as described by Merrifield, 85 J. Amer. Chem. Soc. 2149-2154 (1963) (see, Stemmer et al, 164 Gene 49 (1995)). Synthetic genes, the in vitro or in vivo transcription and translation of which will result in the production of the desired secreted factor protein can be constructed by techniques well known in the art (see Brown et al., 68 Methods in Enzymology 109-151 (1979)). The coding polynucleotide can be generated using conventional DNA synthesizing apparatus such as the Applied Biosystems Model 380A or 380B DNA synthesizers (commercially available from Applied Biosystems, Inc., 850 Lincoln Center Drive, Foster City, Calif. USA).

Briefly, construction of recombinant expression vectors employs standard ligation techniques. For analysis to confirm correct sequences in vectors constructed, the genes are sequences using, for example, the method of Messing, et al., (Nucleic Acids Res., 9: 309-, 1981), the method of Maxam, et al., (Methods in Enzymology, 65: 499, 1980), or other suitable methods which will be known to those skilled in the art.

Size separation of cleaved fragments is performed using conventional gel electrophoresis as described, for example, by Maniatis, et al., (Molecular Cloning, pp. 133-134, 1982).

The term "biological agent" refers to any agent, such as a virus, protein, peptide, amino acid, lipid, carbohydrate, nucleic acid, nucleotide, drug, pro-drug or other substance that may have an effect on neural cells whether such effect is harmful, beneficial, or otherwise. Biological agents that are beneficial to neural cells are "neurological agents", a term which encompasses any biologically or pharmaceutically active substance that may prove potentially useful for the proliferation, differentiation or functioning of CNS or eye cells or treatment of neurological or opthalmological disease or disorder. For example, the term may encompass certain neurotransmitters, neurotransmitter receptors, growth factors, growth factor receptors, and the like, as well as enzymes used in the synthesis of these agents.

When the genetic modification is for the production of a biological agent, the substance can be one that is useful for the treatment of a given disorder such as a CNS disorder. Cells can be genetically modified to express a biologically active agent, such as growth factors, growth factor receptors, neurotransmitters, neurotransmitter synthesizing genes, neuropeptides, and chromaffin granule amine transporter. For example, it may be desired to genetically modify cells so they secrete a proliferation-inducing growth factor or a differentiation-inducing growth factor.

The biological agent can be basic fibroblast growth factor (bFGF), acid fibroblast growth factor, epidermal growth factor, transforming growth factor a, transforming growth factor [3, nerve growth factor, insulin like growth factor, platelet derived growth factor, glia cell line-derived neurotrophic factor, neurturin, persephin, Neublastin (Artemin), brain derived neurotrophic factor, ciliary neurotrophic factor, phorbol 12-myristate 13-acetate, tryophotin, activin, thyrotropin releasing hormone, interleukins, bone morphogenic protein, macrophage inflammatory proteins, heparin sulfate, amphiregulin, retinoic acid, tumor necrosis factor a, fibroblast growth factor receptor, epidermal growth factor receptor, or other agents expected to have therapeutically useful effects on potential target tissues. Examples of biological agents include trophic factors such as glial-derived neurotrophic factor (GDNF), neurturin, arternin and persephin; regulators of intracellular pathways associated with growth factor activity such as staurosporine, CGP-4 1251, and the like; hormones; various proteins and polypeptides such as interleukins; heparin-like molecules; antibodies such as human antibodies, humanised antibodies, chimeric antibodies, antigen binding fragments of antibodies such as Fv, scFv, Fab, Fab' or F(ab)2, as well as multimeric forms such as dimeric IgA molecules or pentavalent IgM, affibodies and diabodies and a variety of other molecules that have an effect on target cells such as neural cells.

In another embodiment, the secreted biologically active compound is a small molecule synthesised by the cells. In these embodiments the structural gene codes for a polypeptide involved in the biosynthesis of a small molecule. One example involves expression of enzymes for dopamine synthesis including AADC (aromatic amino acid decarboxylase), TH (tyrosine hydroxylase) and GCHl (GTP-cyclohydrolase 1). Another example involves expression of an enzyme for GABA synthesis including GAD (Glutamic acid decarboxylase).

In other embodiments, the expression of a gene is down-regulated using siRNA technology. This may under certain circumstances lead to increased secretion of a biologically active compound. For example the structural gene may code for siRNA order to downregulate an endogenous protein, such as adenosine kinase in order to promote adenosine synthesis and secretion.

Mammalian cells can be engineered to produce various neurotransmitters or their receptors such as serotonin, L-dopa, dopamine, norepinephrine, epinephrine, tachykinin, substance P, endorphin, enkephalin, histamine, N-methyl D-aspartate, glycine, glutamate, GABA, ACh, and the like. Useful neurotransmitter-synthesizing genes include TH, DDC, DBH, PNMT, GAD, tryptophanhydroxylase, ChAT, and histidine decarboxylase. Genes that encode for various neuropeptides, which may prove useful in the treatment of CNS disorders, include substance-P, neuropeptide-Y, galanin, enkephalin, vasopressin, VIP, glucagon, bombesin, CCK, somatostatin, calcitonin gene-related peptide, and the like.

The effects of the biological agents on cells of the CNS or eye in the recipient host can be identified in vitro based upon significant differences between model cell cultures for central nervous system cells (such as rat pheochromocytoma PC12 cells, cultured primary central nervous neurons, etc.); or eye cells (such as the IO/LD7/4 cell line, ARPE-19 cells, cultured retinal pigment epithelial cells, etc.) relative to control cultures with respect to criteria such as the ratios of expressed phenotypes (neurons, glial cells, or neurotransmitters or other markers), cell viability and alterations in gene expression.

Physical characteristics of the cells can be analyzed by observing cell and neurite morphology and growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (H PLC), Western blots, and radioimmune assays (RIA). Nucleic acid analysis such as Northern blots and PCR can be used to examine the levels of mRNA coding for these molecules, or for enzymes which synthesize these molecules. Also, the cellular detection of transcripts of the desired secreted factor in vivo can be demonstrated by immunochemistry or by other immunological methods.

Support Matrix for Biologically Active Compound Producing Cells

The method of the present invention further comprises the culturing of the biologically active compound producing cells in vitro on a support matrix prior to implantation into the mammalian brain. The preadhesion of cells to microcarriers prior to implantation in the brain is designed to enhance the long-term viability of the transplanted cells and provide long term functional benefit. Methods for culturing cells on a support matrix and methods for implanting said cells into the brain are described in U.S. Pat. No. 5,750,103 (incorporated by reference).

To increase the long term viability of the transplanted cells, i.e., transplanted biologically active compound secreting cells, the cells to be transplanted can be attached in vitro to a support matrix prior to transplantation. Materials of which the support matrix can be comprised include those materials to which cells adhere following in vitro incubation, and on which cells can grow, and which can be implanted into the mammalian body without producing a toxic reaction, or an inflammatory reaction which would destroy the implanted cells or otherwise interfere with their biological or therapeutic activity. Such materials may be synthetic or natural chemical substances, or substances having a biological origin.

The matrix materials include, but are not limited to, glass and other silicon oxides, polystyrene, polypropylene, polyethylene, polyvinylidene fluoride, polyurethane, polyalginate, polysulphone, polyvinyl alcohol, acrylonitrile polymers, polyacrylamide, polycarbonate, polypentent, nylon, amylases, natural and modified gelatin and natural and codified collagen, natural and modified polysaccharides, including dextrans and celluloses (e.g., nitrocellulose), agar, and magnetite. Either resorbable or non-resorbable materials may be used. Also intended are extracellular matrix materials, which are well-known in the art. Extracellular matrix materials may be obtained commercially or prepared by growing cells which secrete such a matrix, removing the secreting cells, and allowing the cells which are to be transplanted to interact with and adhere to the matrix. The matrix material on which the cells to be implanted grow, or with which the cells are mixed, may be an indigenous product of RPE cells. Thus, for example, the matrix material may be extracellular matrix or basement membrane material, which is produced and secreted by RPE cells to be implanted.

To improve cell adhesion, survival and function, the solid matrix may optionally be coated on its external surface with factors known in the art to promote cell adhesion, growth or survival. Such factors include cell adhesion molecules, extracellular matrix, such as, for example, fibronectin, laminin, collagen, elastin, glycosaminoglycans, or proteoglycans or growth factors.

Alternatively, if the solid matrix to which the implanted cells are attached is constructed of porous material, the growth- or survival promoting factor or factors may be incorporated into the matrix material, from which they would be slowly released after implantation in vivo.

When attached to the support according to the present invention, the cells used for transplantation are generally on the "outer surface" of the support. The support may be solid or porous. However, even in a porous support, the cells are in direct contact with the external milieu without an intervening membrane or other barrier. Thus, according to the present invention, the cells are considered to be on the "outer surface" of the support even though the surface to which they adhere may be in the form of internal folds or convolutions of the porous support material which are not at the exterior of the particle or bead itself.

The configuration of the support is preferably spherical, as in a bead, but may be cylindrical, elliptical, a flat sheet or strip, a needle or pin shape, and the like. A preferred form of support matrix is a glass bead. Another preferred head is a polystyrene bead.

Bead sizes may range from about 10 pm to 1 mm in diameter, preferably from about 90 pm to about 150 pm. For a description of various microcarrier beads, see, for example, Fisher Biotech Source 87-88, Fisher Scientific Co., 1987, pp. 72-75; Sigma Cell Culture Catalog, Sigma Chemical Co., St, Louis, 1991, pp. 162-163; Ventrex Product Catalog, Ventrex Laboratories, 1989; these references are hereby incorporated by reference. The upper limit of the bead's size may be dictated by the bead's stimulation of undesired host reactions, which may interfere with the function of the transplanted cells or cause damage to the surrounding tissue. The upper limit of the bead's size may also be dictated by the method of administration. Such limitations are readily determinable by one of skill in the art.
Therapeutic Usefulness of Polymer Encapsulated Cell Delivery of Biologically Active Compounds.

The central nervous system is a site that is subject to chronic degeneration. Growth factors are known to have a tremendous therapeutic potential for treating neuro-degenerative disorders. For example, polymer-encapsulated xenogeneic cells that have been genetically engineered to secrete growth factors can protect against lesion-induced cell loss in the central nervous system in rats (Winn et al., 91 Proc. Natl. Acad. Sci. USA 2324-8 (1994)), primates (Emerich et al., 349 J. Comp. Neurol. 148-64 (1994)), and aged primates (Kordower et al., 91 Proc. Natl. Acad. Sci. USA 10898-902 (1994)), Therapeutic effects have been produced with polymer-encapsulated cell devices directly delivering various growth factors to a range of target sites in the central nervous system with no evidence of adverse effects (Emerich et al., 130 Exp. Neurol. 141-50 (1994), Emerich et al, 736 Brain Res. 99-110 (1996), Emerich et al., 349 J. Comp. Neurol. 148-64 (1994), Hoffman et al., 122 Exp. Neurol. 100-6 (1993), Kordower et al., 72 Neuroscience 63-77 (1996), Kordower et al., 91 Proc. Natl. Acad. Sci. USA 10898-902 (1994), Winn et al., 91 Proc. Natl. Acad. Sci. USA 2324-8 (1994)). The safety of polymer-encapsulated cell delivery of growth factors is supported by studies that found no adverse effects in animals receiving growth factors delivered to the brain for up to one year (Lindner et al., 5 Cell Transplant. 205-23 (1996), Winn et al., 140 Exp. Neurol. 126-38 (1996)). These studies found no adverse effects even in tests of learned behaviors, which are extremely sensitive to neurotoxicity.
Microcapsules In addition to the macrocapsules described above, the neuropeptide secreting cells of the present invention may be encapsulated in microcapsules or microspheres. A microcapsule in the present invention is a capsule having a volume of less than 1 pL.

Microcapsules or microspheres as defined herein are capsules holding less than $10^4$ cells per capsule. Microcapsules may contain substantially less than $10^4$ cells, such as less than 1000 cells per capsule for example less than 100 cells per capsule, such as less than 50 cells per capsule, for example less than 10 cells per capsule, such as less than 5 cells per capsule. Such microcapsules may be structurally relatively simple in that they contain cells dispersed more or less uniformly inside a matrix. Microcapsules may also be coated to provide a more two-layered structure and to ensure that no cells project through the surface of the microcapsules.

As the microcapsules typically are small diameter typically less than 500 pm, such as less than 450 pm, for example less than 400 pm, such as less than 350 pm, for example less than 300 pm, such as less than 250 pm, for example less than 200 pm, such as less than 150 pm, for example less than 100 pm, such as less than 50 pm, for example less than 25 pm, such as less than 20 pm, for example less than 10 pm, such as less than 5 pm they can be handled like a liquid suspension and be injected at a treatment site.
Suicide Systems The devices of the present invention, which encapsulate biologically active compound-secreting cells, may be retrieved from the patient when required. As a further safety precaution the cells may be equipped with a suicide system, which ensures that the cells may be selectively killed upon administration of a suitable drug to the patient in question.

The suicide system is particularly preferred for naked cell transplantation according to the present invention, as the possibilities for removing naked cells after transplantation are very limited.

One such suicide system is based on thymidine kinases. By having a built-in suicide system in which a thymidine kinase is expressed constitutively or inducibly, the cells can be killed by administering to the individual a therapeutically effective amount of a nucleoside analog, such as AZT. The nucleoside analogue can be administered if the encapsulated cells start to proliferate in an uncontrolled manner. One may also wish to terminate the treatment simply because there is no need for the biologically active compound-secreting cells anymore, because termination must be immediate and cannot await surgical removal of the encapsulated cells or because further treatment is by some other route.

In the cases where transplanted or encapsulated cells have been conditionally immortalised before transplantation there is a theoretical risk that the oncogene initiates transcription after transplantation and that the transplanted cells consequently become tumorigenic. Whenever cells are immortalised by transduction with an oncogene under the control of an inducible promoter (e.g. the Tet on-off system, the Mx1 promoter or the like), a thymidine kinase (TK) enzyme coding sequence is inserted into the vector construct under the control of the same promoter (e.g. by using an IRES construct) or the TK coding sequence is inserted into another vector with an identical promoter. This ensures that whenever the oncogene is transcribed, the TK is also transcribed and the transduced and tumorigenic cells can be selectively killed by administering a prodrug.

There are several examples of thymidine kinase (TK) genes described in the art. One preferred TK is the HSV-thymidine kinase. Other preferred kinases include *Drosophila melanogaster* thymidine kinase described in Munch-Petersen et al 2000, J. Biol. Chem. 275:6673-6679. Mutants of this particular kinase are even more preferred as they have decreased $LD_{50}$ with respect to several nucleoside analogues (WO 01/88106). Another group of preferred thymidine kinases include plant kinases described in WO 03/100045.
Immunostimulatory Cell Surface Proteins In one embodiment there is provided encapsulated human cells capable of expressing an immunostimulatory cell surface polypeptide in addition to the biologically active compound. These immunostimulatory cell surface expressing cells are particularly useful when encapsulated for implantation in a human patient, because cells escaping from a ruptured capsule are destroyed by the patient's immune system. A host immune response will not be triggered by the recombinant cells expressing an immunostimulatory cell surface polypeptide in an intact device. In case of a device failure, however, the released cells are effectively eliminated by phagocytes without complement activation or the creation of an immune memory.

In a specific embodiment, a chimeric polypeptide containing the human transferrin receptor membrane domain anchors a human IgG, Fe to the surface of the cell plasma membrane in a "reversed orientation", thus mimicking the configuration of IgG during opsonisation. The human IgG, chimeric polypeptide binds the Fe receptor to activate phagocytes, such as macrophages, but avoids the undesirable characteristics of also activating the complement cascade ("complement fixation"). A chronically activated complement system can kill host cells, and accumulating evidence suggests that this mechanism can cause many degenerative diseases, including inflammation and neurodegenerative diseases. Further details of this embodiment of the invention are described in U.S. Pat. No. 6,197,294 (Neurotech)

According to this embodiment the cell line further comprises a construct comprising a promoter operatively linked to a polynucleotide sequence encoding a fusion protein comprising an immunostimulatory cell surface protein linked at the amino terminus to a second cell surface polypeptide, wherein the second cell surface polypeptide comprises a transmembrane region, wherein upon expression, the fusion protein is expressed on the cell surface.

Preferably the immunostimulatory cell surface polypeptide activates phagocytes but does not fix complement. In one embodiment the immunostimulatory cell surface polypeptide is a region of IgG, preferably Fe. The second cell surface polypeptide may be a transferrin receptor hinge region.

EXAMPLES

Example 1

Construction of Galanin and NGF Expression Plasmids and Sub-Cloning of the Expression Cassettes into the Substrate Vector of the Sleeping Beauty Transposase for Production of Wt Galanin and Wt NGF by Mammalian Cells 1) The galanin constructs were made as follows: IgSP-deltaprepro-galanin was generated by overlapping PCR. In the first amplification step the galanin sequence coding for mature galanin and the C-terminal peptide with 10 bp IgSP FLAP (lgSP=mouse lg heavy chain gene V-region signal peptide sequence) was PCR amplified from the pCMV-SPORT6-hgalanin plasmid (obtained from RZPD Berlin, Germany, clone ID: IRATp970F0849D6) using primers FLAP-IgSP-mature gala (SEQ ID NO 10), 5' (5'-GGTGAAT-TCGGGCTGGACCCTGAACAGCGCG-3') and Deltaprepro-galanin-Xhol (SEQ ID NO 11) 3' (5'-TATACTCGAGCAGGAATGGCTGACTCTGCATAAATTGGCC-3'). In a second PCR reaction a fragment containing the full length IgSP sequence with a 10 bp galanin FLAP from the 5' end of mature galanin was amplified from pNUT-IgSP-hCNTF (U.S. Pat. No. 6,361,771) using primers IgSPkozakls+BamHI (SEQ ID NO 12) (5'-TATAGGATCCGCCACCATGAAATGCAGCTGGGTTATC-3') and IgSP-galanin FLAP as (SEQ ID NO 13) (5'-GGGTCCAGCCCGAATTCACCCCTGTAGAAAG-3'). In the third step the products of step 1 and 2 were combined in a final PCR reaction that generated the IgSP-deltaprepro-galanin fragment by using equimolar amounts of products of the first two PCR reactions and the primers IgSPkozakls+BamHI and Deltaprepro-galanin-Xhol 3'.

To generate a plasmid-based expression vector the resulting PCR fragment was cloned into pCAn digested with BamHI/Xhol. The pCAn vector is derived from pcDNA3.1 (invitrogen). The CMV promoter was removed from pcDNA3.1 and replaced with the human CMV enhancer/chicken beta-actin (CAG) promoter and first intron. Furthermore, the vector contains the Neogene that confers 0418 resistance when expressed in mammalian cells. The IgSP-deltaprepro-galanin fragment expression cassette (i.e. including the CAG promoter as well as neomycin resistance expression cassette) was then sub-cloned from the pCAn vector into plasmid pT2BH. pT2BH is the substrate vector for the transposase Sleeping Beauty (Ivies et al., Cell, 91: 501-10 (1997)). The sub-cloning was done by first digesting pT2BH with Bglll and EcoRV. The pCAn-IgSP-deltaprepro-galanin vector was then digested with BsmBl followed by fill-in reaction with Klenow large fragment polymerase. The blunted, opened vector was then digested with Bglll to create a semi-blunt IgSP-deltaprepro-galanin+neomycn resistance expression cassette fragment, which was cloned into the Bglll-EcoRV-digested pT2BH vector.

2) The Human NGF constructs were made as follows: human preproNGF was PCR amplified from genomic DNA isolated from HEK293 cells using the following primers: hNGFs+BamHl (SEQ ID NO 14): 5'-TATAGGATCCCTCTGAGGGACCCAGAAACT-3' and hNGFas+Xhol (SEQ ID NO 15): 5'-TATACTCGAGCAGGTCAGGCTCTTCTCAC-3'. The resulting PCR fragment was cut with BamHI and Xhol and inserted into BamHl and Xhol sites of the expression vector pCAn (described above) to generate the construct pCAn.hNGF. The expression cassette from pCAn.hNGF (also containing the neomycin resistance cassette) was excised as a semi-blunt fragment using Bglll and SsPI. The Sleeping Beauty transposase substrate vector, pT2BH, was digested with Bglll and EcoRV. The CAn.hNGF fragment was ligated into the Bglll and EcoRV digested vector backbone to create the construct pT2.CAn.hNGF.

Sequences from the constructs are shown in Example 2.

Example 2. Sequences of the constructs described in Example 1
IqSP-deltaprepro-galanin nucleotide sequence present in
constructs pCAn.IgSP-deltaprepro-galanin and pT2.CAn.IgSP-
deltaprepro-galanin (SEQ ID NO 1)
ATGAAGTGCAGCTGGGTGATCTTCTTCCTGATGGCAGTGGTTACAGGTAAGGGGCTCCCA
AGTCCCAAACTTGAGGGTCCATAAACTCTGTGACAGTGGCAATCACTTTGCCTTTCTTTC
TACAGGGGTGAATTCGGGCTGGACCCTGAACAGCGCGGGCTACCTGCTGGGCCCTCACGC
CGTGGGCAACCACAGAAGCTTCAGCGACAAGAACGGCCTGACCAGCAAGCGGGAGCTGCG
GCCCGAGGACGACATGAAGCCCGGCAGCTTCGACAGAAGCATCCCCGAGAACAACATCAT

```
GCGGACCATCATCGAGTTTCTGAGCTTTCTGCACCTGAAAGAGGCCGGAGCCCTGGACCG
GCTGCTGGATCTGCCTGCCGCTGCCTCCTCAGAAGACATCGAGCGGTCCTGA
```
IgSP-deltaprepro-galanin is the mouse Ig heavy chain gene V-region
signal peptide (GenBank ID: M18950) fused to human galanin devoid
of the prepro sequence but including the C-terminal tail. Note
that the IgSP-deltaprepro-galanin sequence contains an intron.

Translation of IgSP-galanin transcript
(SEQ ID NO 2)
```
MKCSWVIFFLMAVVTGVNSGWTLNSAGYLLGPHAVGNHRSFSDKNGLTSKRELRPEDDMKPGSF
DRSIPENNIMRTIIEFLSFLHLKEAGALDRLLDLPAAASSEDIERS
```
The mature galanin sequence is accentuated in bold.

Human preproNGF nucleotide sequence present in constructs
pCAn.hNGF and pT2.CAn.hNGF
(SEQ ID NO 3)
```
ATGTCCATGTTGTTCTACACTCTGATCACAGCTTTTCTGATCGGCATACAGGCGGAACCA
CACTCAGAGAGCAATGTCCCTGCAGGACACACCATCCCCCAAGTCCACTGGACTAAACTT
CAGCATTCCCTTGACACTGCCCTTCGCAGAGCCCGCAGCGCCCCGGCAGCGGCGATAGCT
GCACGCGTGGCGGGGCAGACCCGCAACATTACTGTGGACCCCAGGCTGTTTAAAAAGCGG
CGACTCCGTTCACCCCGTGTGCTGTTTAGCACCCAGCCTCCCCGTGAAGCTGCAGACACT
CAGGATCTGGACTTCGAGGTCGGTGGTGCTGCCCCCTTCAACAGGACTCACAGGAGCAAG
CGGTCATCATCCCATCCCATCTTCCACAGGGGCGAATTCTCGGTGTGTGACAGTGTCAGC
GTGTGGGTTGGGGATAAGACCACCGCCACAGACATCAAGGGCAAGGAGGTGATGGTGTTG
GGAGAGGTGAACATTAACAACAGTGTATTCAAACAGTACTTTTTTGAGACCAAGTGCCGG
GACCCAAATCCCGTTGACAGCGGGTGCCGGGGCATTGACTCAAAGCACTGGAACTCATAT
TGTACCACGACTCACACCTTTGTCAAGGCGCTGACCATGGATGGCAAGCAGGCTGCCTGG
CGGTTTATCCGGATAGATACGGCCTGTGTGTGTGCTCAGCAGGAAGGCTGTGAGAAGA
GCCTGA
```

Translation of human preproNGF transcript
(SEQ ID NO 4)
```
MSMLFYTLITAFLIGIQAEPHSESNVPAGHTIPQVHWTKLQHSLDTALRRARSAPAAAIA
ARVAGQTRNITVDPRLFKKRRLRSPRVLFSTQPPREAADTQDLDFEVGGAAPFNRTHRSK
RSSSHPIFHRGEFSVCDSVSVWVGDKTTATDIKGKEVMVLGEVNINNSVFKQYFFETKCR
DPNPVDSGCRGIDSKHWNSYCTTTHTFVKALTMDGKQAAWRFIRIDTACVCVLSRKAVRRA
```
The mature NGF sequence is accentuated in bold.

IR/DR (L) left hand (complementary strand) Sleeping Beauty (SB)
substrate sequence present in pT2-derived constructs
(SEQ ID NO 5)
```
CAGTTGAAGTCGGAAGTTTACATACACTTAAGTTGGAGTCATTAAAACTCGTTTTTCAAC
TACTCCACAAATTTCTTGTTAACAAACAATAGTTTTGGCAAGTCAGTTAGGACATCTACT
TTGTGCATGACACAAGTCATTTTTCCAACAATTGTTTACAGACAGATTATTTCACTTATA
ATTCACTGTATCACAATTCCAGTGGGTCAGAAGTTTACATACACTAA
``` preproNGF
(SEQ ID NO 6)
```
CAGTTGAAGTCGGAAGTTTACATACACTTAAGTTGGAGTCATTAAAACTCGTTTTTCAAC
TACTCCACAAATTTCTTGTTAACAAACAATAGTTTTGGCAAGTCAGTTAGGACATCTACT
TTGTGCATGACACAAGTCATTTTTCCAACAATTGTTTACAGACAGATTATTTCACTTATA
ATTCACTGTATCACAATTCCAGTGGGTCAGAAGTTTACATACACTAA
```

IR/DR (R) right hand SB substrate sequence present in pT2-derived
constructs
(SEQ ID NO ]J_
```
TTGAGTGTATGTAAACTTCTGACCCACTGGGAATGTGATGAAAGAAATAAAAGCTGAAAT
GAATCATTCTCTCTACTATTATTCTGATATTTCACATTCTTAAAATAAAGTGGTGATCCT
AACTGACCTAAGACAGGGAATTTTTACTAGGATTAAATGTCAGGAATTGTGAAAAAGTGA
GTTTAAATGTATTTGGCTAAGGTGTATGTAAACTTCCGACCTTCAACTG
```

Protein sequence of SB transposase SB10 (wt Sleeping Beauty
transposase)
(SEQ ID NO 8)

```
MGKSKEISQD LRKRIVDLHK SGSSLGAISK RLKVPRSSVQ TIVRKYKHHG
TTQPSYRSGR RRVLSPRDER TLVRKVQINP RTTAKDLVKM LEETGTKVSI
STVKRVLYRH NLKGHSARKK PLLQNRHKKA RLRFATAHGD KDRTFWRNVL
WSDETKIELF GHNDHRYVWR KKGEACKPKN TIPTVKHGGG SIMLWGCFAA
GGTGALHKID GIMRKENYVD ILKQHLKTSV RKLKLGRKWV FQMDNDPKHT
SKVVAKWLKD NKVKVLEWPS QSPDLNPIEN LWAELKKRVR ARRPTNLTQL
HQLCQEEWAK IHPTYCGKLV EGYPKRLTQV KQFKGNATKY
```
Mutations are accentuated in bold and underlined.

Protein sequence of hyperactive SB transposase SB100x
(SEQ ID NO 10)
```
MGKSKEISQD LRKRIVDLHK SGSSLGAISK RLAVPRSSVQ TIVRKYKHHG
TTQPSYRSGR RRVLSPRDER TLVRKVQINP RTTAKDLVKM LEETGTKVSI
STVKRVLYRH NLKGHSARKK PLLQNRHKKA RLRFATAHGD KDRTFWRNVL
WSDETKIELF GHNDHRYVWR KKGEACKPKN TIPTVKHGGG SIMLWGCFAA
GGTGALHKID GIMDANNYVD ILKQHLKTSV RKLKLGRKWV FQHDNDPKHT
```

```
-continued
SKVVAKWLKD NKVKVLEWPS QSPDLNPIEN LWAELKKRVR ARRPTNLTQL
HQLCQEEWAK IHPNYCGKLV EGYPKRLTQV KQFKGNATKY
Mutations are accentuated in bold and underlined.
```

Example 3. Generation of Stable Galanin- and NGF-Secreting Mammalian Cells and Comparison of Levels of Secreted Neuropeptides Production of Stable Cell Lines in ARPE-19 Cells Using the Constructs Described in Example 1

ARPE-19 is a human retinal pigment epithelial cell line (Dunn et al. 1996) grown in DMEM/Nutrient Mix F-12 with Glutamax (invitrogen, Denmark) supplemented with 10% fetal bovine serum (Sigma-Aldrich, Denmark) at 37° C. and 5% CO2. Cells were passaged approximately twice a week by trypsinization and reseeding (1:5 split ratio). Cells were seeded in T150 flasks (Corning Costar, Biotech Line, Denmark) at a density of $2.4 \times 10^6$ cells/flask for transfection studies. The next day, cells in each flask were co-transfected with pT2 SB substrate vector containing galanin or NGF expression cassettes and the SB-lOOx hyperactive transposase expression vector using either a 3:1 ratio (7.5 pg pT2 vector and 2.5 pg SB-lOOx) or a 10:1 ratio (9 pg pT2 vector and 0.9 pg SB-lOOx) using Fugene6 (Roche, Germany) according to the manufacturer's specifications. To select for stable transfectants, 48 hours post-transfection 800 pg/ml 0418 was added to the culture medium. When clones appeared to be well-defined and separated from each other, approximately 200 clones from each construct were picked and transferred to 48 well plates. When confluent in these plates, galanin clones were tested for the presence of galanin using a commercial galanin ELISA kit (cat. #S-1210, Bachem) and NGF clones were tested for the presence of NGF using a commercial NG F ELISA Kit (NGF Duoset, R&D Systems). The highest producing clones were further expanded in T150 flasks and aliquots were frozen in liquid N2.

Results

Galanin and NGF Secretion from pCAn-Based and pT2-Based Clones In Vitro

The best galanin and NGF clones were subjected to expression stability studies in culture for up to 8 weeks (2D studies). From FIG. 1 it is clear that clones generated using the SB transposase system secrete surprisingly large amounts of factor as compared to clones generated by standard transfection.

Galanin Secretion from pCAn-Based and pT2-Based Clones In Vivo

Figure 2:
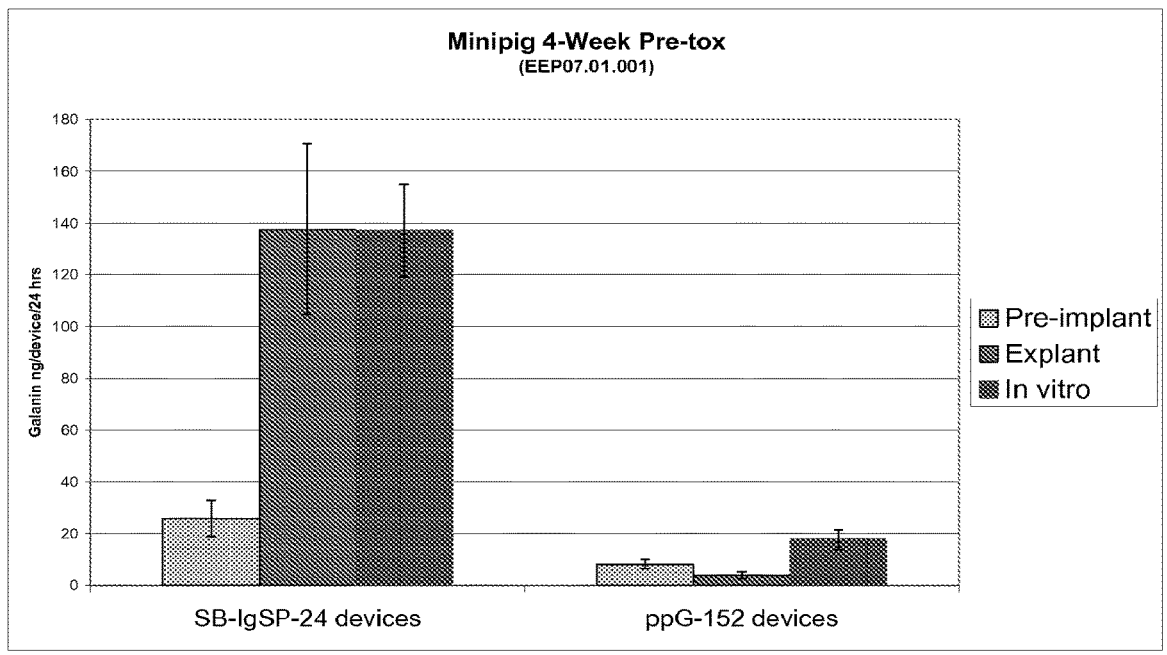
FIG. 2: Galanin 4-week in vivo study in minipigs. Galanin expression levels of encapsulated SB-galanin clone, SB-IgSP-24, made using the SB technology versus clone ppG-152, made using standard transfection techniques. Pre-implantation values (blue bars) are compared to explant values (red bars) and devices run in vitro in parallel (yeallow bars). Devices were implanted into the hippocapmus of the minipigs.

The most stable of galanin high (SB-IgSP-24) and low (ppG-152) producer clones from the 2D-study were tested for expression stability in vivo in the Goettingen minipig model. The clones were encapsulated using NsGene's proprietary Encapsulated Cell (EC) Biodelivery technology. In short, 14 mm polyether-sulphone (PES) membranes with a molecular weight cut-off (MWCO) of 280 kD were filled with 250,000 cells/device. Cells were allowed to settle and propagate om devices for 2 weeks before implantation in the hippocampus of the pigs. Devices were explanted after 4 weeks. FIG. 2 shows secreted galanin levels from devices before implantation compared to explanted devices and devices run in parallel in vitro. It is clear that the secretion level of galanin from the clone, SB-IgSP-24, produced using the SB technology, is unexpectedly large as compared to the clone, ppG-152, generated using standard transfection techniques (explant levels: appr. 150 ng/device/24 hrs vs. 5 ng/device/24 hrs).

NGF Secretion from pCAn-Based and pT2-Based Clones In Vivo

Figure 3:
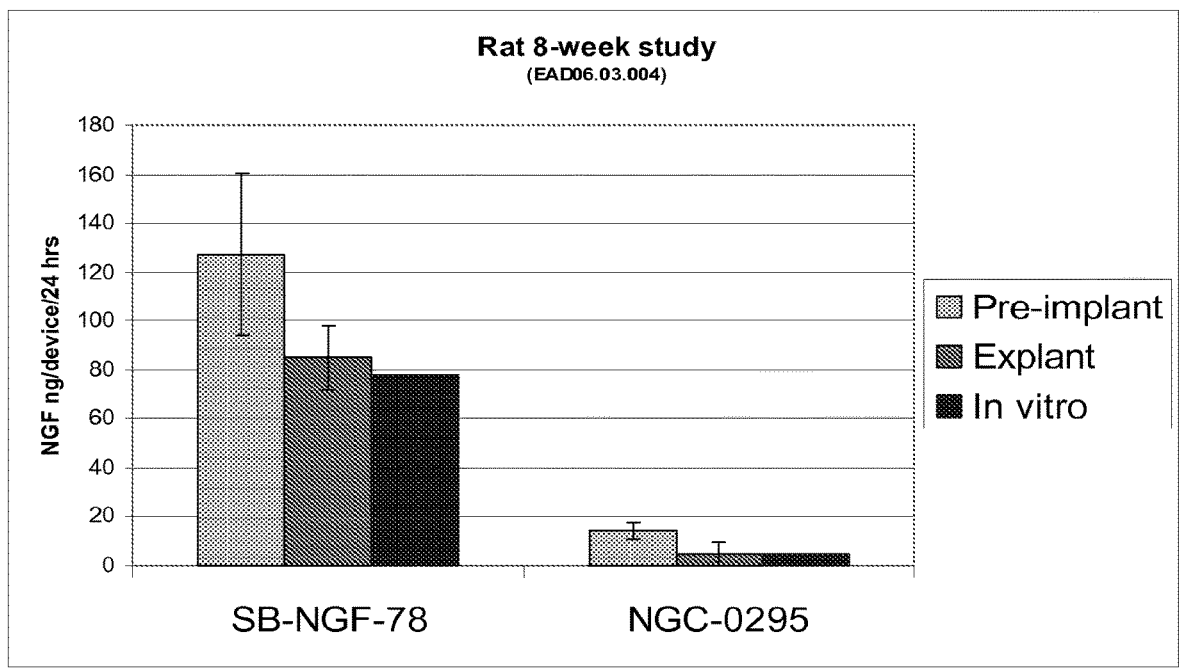
FIG. 3: NGF 8-week in vivo study in rats. NGF expression levels of encapsulated SB-galanin clone, SB-NGF-78, made using the SB technology versus clone NGC-0295, made using standard transfection techniques. Pre-implantation values (blue bars) are compared to explant values (red bars) and devices run in vitro in parallel (yeallow bars). Devices were implanted into the striatum of the rats.

The most stable of NGF high producer clone (SB-NGF-78) from 2D studies and the best low producer clone generated earlier (NGC-0295) were tested for expression stability in vivo in rats. The clones were encapsulated by filling 280 kD MWCO, 7 mm PES membranes with 100,000 cells/device using NsGene's proprietary Encapsulated Cell (EC) Biodelivery technology. Devices were implanted in the striatum of the rats and were left for 8 weeks before explantation. FIG. 3 shows secreted NGF levels from devices before implantation compared to explanted devices and devices run in parallel in vitro. The NGF secretion level from clone SB-NGF-78, produced using the SB technology, is unpredictably large as compared to clone NGC-0295, generated using standard transfection techniques (explant levels: appr. 80 ng/device/24 hrs vs. 8 ng/device/24 hrs).

Comparative Example 4: Other Tested Transgene Expression-Enhancing Initiatives

TABLE 1

Schematic presentation of other tested transgene expression enhancing initiatives.

| Enhancement method | Description | Result |
| --- | --- | --- |
| Promoter | CMV—cytomegalovirus<br>CI—CMV promoter + chimeric intron<br>PGK—phosphoglycerate kinase<br>Metallothionein | All promoters tested in constructs similar to the pCAn constructs. Promoters were either weaker than the CA promoter or expression downregulation was pronounced in vivo. |
| Signal peptide (SP) | Lymphotoxin - 34 amino acid SP<br>Semaphorin - 38 amino acid SP<br>Fibronectin - 26 amino acid SP<br>NGF - 121 amino acid prepro region<br>GDNF - 77 amino acid prepro region | The long SPs from lymphotoxin and semaphorin, lead to secreted but incorrectly processed factor. Fibronectin SP as well as NGF and GDNF prepro-regions led to no or low secretion levels of factor. |

TABLE 1-continued

Schematic presentation of other tested transgene expression enhancing initiatives.

| Enhancement method | Description | Result |
|---|---|---|
| Copy number | Methotrexate can be used to amplify gene cassettes containing the mutant dominant dihydrofolate reductase (DHFR) gene. This can be used to create cell clones with multiple copies of an inserted transgene. | The method was unsuccessful in ARPE-19: Cells - transfected with the DHFR cassette-were very difficult to grow in even low amounts of methotrexate. |
| Codon optimization | Conservative codon optimization is commercially available. | Codon optimized galanin and NGF open reading frames have led to an expression increase of several fold. |

Example 5. Determination of Transgene Copy Numbers in Cell Lines Generated Using a Transposase System The technique used for this determination is called transposon display (Wicks et al., Dev. Biol. 221: 295-307 (2000)), which is a derivative from the vectorette method (Hui et al., Cell. Mol. Life Sci. 54: 1403-11 (1998)).

The method in brief: 1) Genomic DNA is prepared from the cell line. 2) The genomic DNA is digested with a restriction enzyme to fragment the chromosomes. 3) A. so called, vectorette linker/cassette of appr. 500 bp—with an overhang matching the overhangs of the genomic DNA created by the restriction enzyme—is ligated to the digested genomic DNA. The vectorette linker contains a central appr. 50 bp mismatch region. 4) A two step vectorette PCR is carried out using a primer annealing to one strand of the vectorette and another primer annealing to a sequence in the transposon.

Due to the mismatch region in the vectorette linker, only fragments containing a vectorette linker ligated to a digested genomic DNA fragment containing a copy of the transgene (surrounded by transposase substrate sequences) will be amplified (see FIG. 1 from Hui et al., Cell. Mol. Life Sci. 54: 1403-11 (1998).

Using this method on galanin and NGF secreting cell lines created with the Sleeping Beauty transposon system, a good correlation between copy number and secretion levels of the transgene factor was found (see table 2). High producer SB clones typically have 1-6 transgene copies of NGF or 1-18 transgene copies of Galanin. Thus, there is to some extent a correlation between number of transgene copies and the observed improvement in factor secretion levels of SB-clones. However, when comparing the factor secretion levels of SB-clones with one transgene copy and the clones generated using standard transfection techniques also containing one copy of the transgene, it is clear that the number of transgene copies is not the only thing determining secretion level and the SB-clones do have a factor secretion level that is higher and more stable than would normally be expected.

CONCLUSION

It is clear from the above tests of SB-derived clones versus clones derived using standard transfection techniques, that the SB system is capable of boosting secretion of the transgene more than would be expected from an increase of 3-5 in transgene copy number in the host cell. In this context it is important to mention that several other potential expression enhancing initiatives have been tested (see table 1 below).

TABLE 2

Comparison of factor secretion levels over a wide range with copy numbers from clones secreting galanin or NGF generated using the Sleeping Beauty transposon system.

| Galanin clones | Galanin ng/ml/24 hrs | Copy number |
|---|---|---|
| SB-IgSP4 | 384 | 5 |
| SB-IgSP5 | 187 | 1 |
| SB-IgSP8 | 600 | 12-13 |
| SB-IgSP11 | 644 | 7-9 |
| SB-IgSP24 | 657 | 9 |
| SB-IgSP41 | 182 | 2-3 |

| NGF clones | NGF ng/ml/24 hrs | |
|---|---|---|
| SB-NGF11 | 622 | 4 |
| SB-NGF29 | 219 | 1 |
| SB-NGF40 | 402 | 2-5 |
| SB-NGF68 | 341 | 1 |
| SB-NGF77 | 355 | 1 |
| SB-NGF78 | 2007 | 6 |

Sequences

| SEQ ID NO | Type | Description |
|---|---|---|
| 1 | N | IgSP-deltaprepro-galanin |
| 2 | P | IgSP-deltaprepro-galanin |
| 3 | N | Human prepro-NGF |
| 4 | P | Human prepro-NGF |
| 5 | N | IR/DR left hand (complementary strand) Sleeping Beauty substrate sequence present in pT2 derived constructs |
| 6 | N | IR/DR right hand Sleeping Beauty substrate sequence present in pT2 derived constructs |
| 7 | P | Sleeping Beauty transposase SB10(wild type Sleeping Beauty transposase) |
| 8 | P | Protein sequence of hyperactive Sleeping Beauty transposase (SB100X) |
| 9 | P | Protein sequence of hyperactive Sleeping Beauty transposase (SB80X) |
| 10 | N | Primer FLAP-IgSP-mature galanin |
| 11 | N | Primer Deltaprepro-galanin-XhoI |
| 12 | N | Primer IgSPkozak1s + BamHI |
| 13 | N | Primer IgSP-galanin FLAP |
| 14 | N | Primer hNGFs + BamHI |
| 15 | N | Primer hNGFas + XhoI |

The invention claimed is:

1. A capsule for delivery of a secreted biologically active compound to a subject, the capsule comprising
   a. a biocompatible outer membrane and an inner core,
   b. said inner core comprising monoclonal cells,
   c. said monoclonal cells comprising a heterologous expression construct comprising a structural gene coding for siRNA contributing to the generation in the cells of a biologically active secreted compound,
   d. said gene being located between two inverted repeats, IR/DR, which are substrates for a transposase or other integrases,
   wherein said monoclonal cells maintain a high and stable expression level of the siRNA absent the presence of a selective pressure compared to the same cells generated without a transposase;
   wherein the thickness of the outer membrane is between 2 and 200 microns;
   wherein said capsule has a volume between 1 μL and 5 μL; and
   further wherein said capsule contains less than $10^3$ monoclonal cells.

2. The capsule according to claim 1, wherein all cells in the device are derived from a single cell line.

3. The capsule according to claim 2, wherein the cell line is selected from the group consisting of a human stem cell line, a human astrocyte cell line, a human mesencephalic cell line, a human epithelial cell line, an ARPE-19 derived cell line and a human monoclonal cell line.

4. The capsule according to claim 1, wherein the expression construct comprises a constitutive promoter selected from the group consisting of CAG, CMV, human Ubic, JeT, RSV, EF-lalpha, SV40 and Mt1.

5. The capsule according to claim 1, wherein said promoter is an inducible promoter selected from the group consisting of Tet-On, Tet-Off, Mo-MLV-LTR, Mxl, progesterone, RU486 and Rapamycin-inducible promoter.

6. The capsule according to claim 1, wherein the structural gene codes for siRNA in order to downregulate an endogenous protein.

7. The capsule according to claim 6, wherein the endogenous protein is an adenosine kinase designed to promote adenosine synthesis and secretion.

8. The capsule according to claim 1, wherein the expression construct further comprises a sequence selected from the group consisting of: Kozak consensus sequence, WPRE, β-globin insulator, SP163 enhancer, non-translated 5' or 3' prime regions from the tau, TH or APP genes.

9. The capsule according to claim 1, wherein the capsule is capable of secreting a growth factor at a rate ranging from 20 ng/capsule/24 hrs to 200 ng/capsule/24 hrs.

10. The capsule according to claim 1, wherein the capsule is capable of secreting a neuropeptide at a rate ranging from 20 ng/capsule/24 hrs to 200 ng/capsule/24 hrs.

11. The capsule according to claim 1, wherein the copy number of the structural gene is an integer from 1 to 25.

* * * * *